United States Patent
Chhibber et al.

(10) Patent No.: US 7,454,046 B2
(45) Date of Patent: Nov. 18, 2008

(54) METHOD AND SYSTEM FOR ANALYZING SKIN CONDITIONS USING DIGITAL IMAGES

(75) Inventors: Rajeshwar Chhibber, San Jose, CA (US); Ashutosh Chhibber, San Jose, CA (US); Shefali Sharma, Petaluma, CA (US); Shivanjli Sharma, Petaluma, CA (US)

(73) Assignee: BrighTex Bio-Photonics, LLC, San Jose, CA (US)

( * ) Notice: Subject to any disclaimer, the term of this patent is extended or adjusted under 35 U.S.C. 154(b) by 415 days.

(21) Appl. No.: 11/232,452

(22) Filed: Sep. 20, 2005

(65) Prior Publication Data

US 2007/0064985 A1    Mar. 22, 2007

(51) Int. Cl.
*G06K 9/00* (2006.01)
(52) U.S. Cl. .................. 382/128; 382/118; 382/224; 600/306; 600/473; 600/476
(58) Field of Classification Search ............... 382/128, 382/118, 224; 600/407, 476, 477, 478, 306, 600/473
See application file for complete search history.

(56) References Cited

U.S. PATENT DOCUMENTS

| | | | |
|---|---|---|---|
| 4,894,547 A | | 1/1990 | Leffell et al. |
| 5,074,306 A | | 12/1991 | Green et al. |
| 5,343,536 A | | 8/1994 | Groh |
| 5,836,872 A | | 11/1998 | Kenet et al. |
| 6,069,689 A | * | 5/2000 | Zeng et al. .................. 356/73 |
| 6,571,003 B1 | | 5/2003 | Hillebrand et al. |
| 6,587,711 B1 | * | 7/2003 | Alfano et al. ............... 600/476 |
| 6,763,262 B2 | * | 7/2004 | Hohla et al. ................ 600/476 |
| 7,369,692 B2 | * | 5/2008 | Shirai et al. ................ 382/128 |
| 2004/0125996 A1 | * | 7/2004 | Eddowes et al. ............ 382/128 |
| 2004/0202685 A1 | | 10/2004 | Manzo |
| 2004/0218810 A1 | | 11/2004 | Momma |
| 2007/0002479 A1 | * | 1/2007 | Menke et al. ............... 359/892 |
| 2007/0064978 A1 | * | 3/2007 | Chhibber et al. ............ 382/118 |
| 2007/0064979 A1 | * | 3/2007 | Chhibber et al. ............ 382/118 |
| 2007/0064985 A1 | * | 3/2007 | Chhibber et al. ............ 382/128 |
| 2007/0064989 A1 | * | 3/2007 | Chhibber et al. ............ 382/128 |

OTHER PUBLICATIONS

Liangen, Zhu et al., "*Human Skin Surface Evaluation by Image Processing*", Proceedings of SPIE, vol. 5254, Third International Conference on Photonics and Imaging in Biology and Medicine, (2003) pp. 362-367.

(Continued)

*Primary Examiner*—Gregory M Desire
(74) *Attorney, Agent, or Firm*—Morgan Lewis & Bockius LLP; Richard F. Trecartin

(57) ABSTRACT

The embodiments of the present invention include a method and system for analyzing skin conditions using digital images. The method comprises acquiring a white-light image and an ultraviolet (UV) image of a portion of a body surface, such as a person's face, each of the white-light and UV images including a plurality of pixels and each pixel in the UV image corresponding to a respective pixel in the white-light image. The method further comprises identifying skin-pixels in the white-light and UV images, and obtaining results associated with at least one skin condition using information in the skin pixels in the first white light and UV images.

40 Claims, 22 Drawing Sheets

OTHER PUBLICATIONS

Sandby-Moller, Jane, "*Influence Of Epidermal Thickness, Pigmentation And Redness On Skin Autofluorescence [para]*" American Society of Photobiology, (Jun. 2003) pp. 1-9.

Sboner, Andrea et al., "*Clinical Validation of an Automated System for Supporting the Early Diagnosis of Melanoma*", Skin Research and Technology (2004) vol. 10, pp. 184-192.

Zeng, Haishan, et al., "*Autofluorescence Properties of Skin and Application in Dermatology*" Proceedings of SPIE, vol. 4224 (2000) pp. 366-373.

International Search Report And the Written Opinion of the International Searching Authority dated Nov. 6, 2007.

* cited by examiner

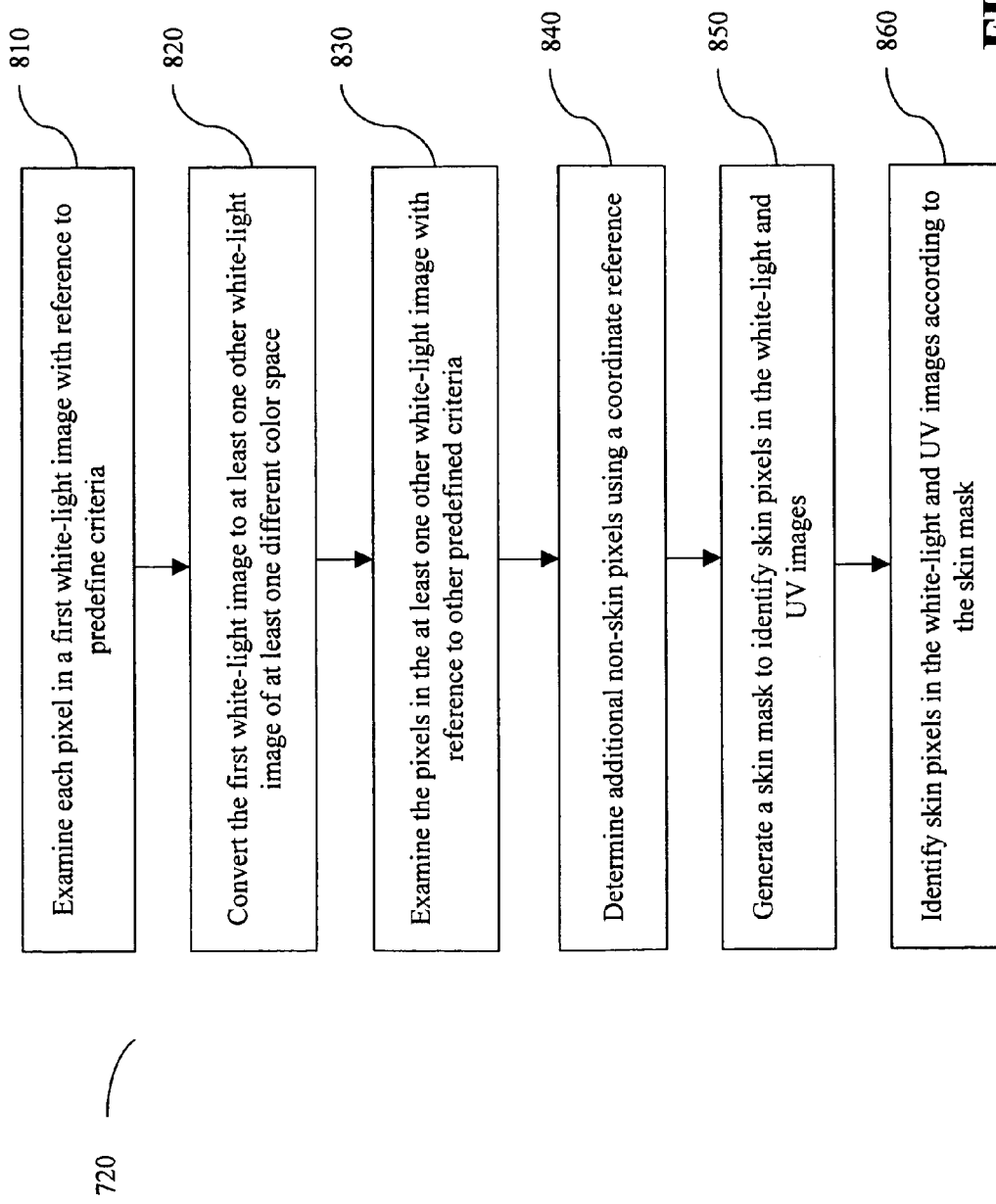

Range for each color channel
likely associated with skin pixel

| Color Space | Channel 1 | Channel 2 | Channel 3 |
|---|---|---|---|
| RGB | 105 – 255 | 52 – 191 | 32 – 180 |
| YIQ | 66 – 206 | 20 – 77 | 0 – 32 |
| LAB | 132 – 165 | 133 – 150 | 170 – 230 |
| YcBcR | 149 – 200 | 85 – 123 | 80 – 190 |
| HSV | 140 – 255 | 62 – 162 | 0 – 41 |

FIG. 9B

| Skin Condition | Color | Values |
|---|---|---|
| Inflamed Pores | White | Intensity greater than 130 |
| Bacteriostatic pores | Yellow | Intensity greater than 130 |
| Sluggish Oil Flow | Red | Intensity greater than 130 |
| Deeply Inflamed Pores | Bright white | Intensity greater than 130 |

FIG. 13B

METHOD AND SYSTEM FOR ANALYZING SKIN CONDITIONS USING DIGITAL IMAGES

CROSS REFERENCE TO RELATED APPLICATIONS

The present application is related to commonly-assigned patent application Ser. No. 11/232,454 entitled "Method and Systems for Automatic Identification Using Digital Images," filed on Sep. 20, 2005, which is incorporated herein by reference in its entirety.

FIELD OF THE INVENTION

The present invention relates in general to digital image acquisition, processing and analysis, and more particularly to analyzing skin conditions by acquiring and processing digital images.

BACKGROUND OF THE INVENTION

Currently, the skin heath care and cosmetic industry produces many different kinds of skin care products, which are sold or administered to customers or patients, relying mainly on qualitative and highly subjective analysis of facial features and skin defects or ailments associated with the customers or patients. The effects of the skin care products are also tested at a qualitative level, without a quantitative and objective proof of effectiveness.

With the recent advancements in digital imaging and microprocessor speed, the medical and healthcare industry are starting to find digital image processing and analysis helpful in the detection or diagnosis of defects or diseases on the surface of or inside the human body or other living organisms. Although several research projects have been carried out in the skin-care industry to explore computer analysis of skin images, the technology of using digital images of a person's skin to evaluate a variety of skin conditions associated with the person is still primitive and in need of substantial development.

SUMMARY

The present invention provides a method and system for analyzing skin conditions using digital images. In one embodiment, the method comprises acquiring a white-light image and an ultraviolet (UV) image of a portion of a body surface, such as a person's face, each of the white-light and UV images including a plurality of pixels and each pixel in the UV image corresponding to a respective pixel in the white-light image. The method further comprises identifying skin-pixels in the white-light and UV images, and obtaining results associated with at least one skin condition using information in the skin pixels in the first white light and UV images.

In one embodiment, the skin pixels are identified by examining each pixel in the white light image and/or UV image to determine if the pixel has properties that satisfy predetermined criteria for skin pixels. Examination of the pixels in the white-light and UV images may include examining with reference to a skin map or skin mask, which is a virtual image or matrix or data group having a plurality of elements, each corresponding to a pixel in the white-light or UV image. In one embodiment, the white-light image is of a first color space, and at least one other white-light image is constructed by converting the original white-light image into at least one second color space. For each element in the skin mask, the corresponding pixel in each of the white light images is examined with reference to predetermined criteria associated with a respective color space. A first value is assigned to an element in the skin mask if the corresponding pixel in each of the white-light images has pixel values that satisfy predetermined criteria for skin pixels associated with a respective color space, and a second value is assigned to an element in the skin mask if the corresponding pixel in any of the white-light images has pixel values that do not satisfy predetermined criteria for skin pixels associated with a respective color space. In a further embodiment, some of the elements in the skin mask are predefined as corresponding to non-skin features according to a coordinate reference. These elements are assigned the second value disregarding what values their corresponding pixels in the white-light images have.

After all elements of the skin mask have been assigned the first or second value, each pixel in any of the white-light and UV images that corresponds to an element having the first value in the skin mask would be identified as a skin pixel, and each pixel in any of the white-light and UV images that corresponds to an element having the second value in the skin mask would be identified as a non-skin pixel. Pixels that are identified as non-skin pixels are not considered in obtaining results for the at least one skin conditions.

In one embodiment, the at least one skin condition includes skin conditions such as skin tone, UV damage, pores, wrinkles, hydration levels, collagen content, and skin type, etc., and the skin pixels of one or both of the first white-light and UV images are processed to obtain the results for the skin conditions.

In one aspect of the invention, each skin pixel of the white-light and UV images includes values associated with three color channels, and the UV damage results are computed based on values associated with one of the three color channels in the skin pixels of the first UV image.

In another aspect, a standard deviation is computed using values associated each of the three color channels in the skin pixels of the white-light image, and the standard deviations for the three color channels, or their average value, is used to as a quantitative measure for the skin tone.

In a further aspect of the present invention, a color value and an intensity value associated with each of the skin pixels in the UV image are computed and examined with reference to at least one look-up table to determine if they correspond to a specified skin condition. For each skin pixel in the UV image that is determined to correspond to a specified skin condition, surrounding skin pixels are examined for the specified skin condition to determine a size of a skin area having the specified skin condition. Statistical results such as a number and/or distribution of the areas having one or more specified skin conditions can also be provided.

In one embodiment, the results associated with at least one selected skin condition can be displayed on a user interface using an image having the at least one type of skin condition highlighted, and/or with at least one number or chart quantifying the skin condition. In a further embodiment, both current and prior results associated with at least one selected skin condition for the person are displayed next to each other for comparison.

According to embodiments of the present invention, the system for analyzing skin conditions generally includes an image acquisition device, at least one light source coupled to the image acquisition device, and a computing device coupled to the image acquisition device and to the light source, and a display coupled to the computing device. The computing device includes modules for carrying out different aspects of the method for analyzing skin conditions as summarized above and described in more detail below. The modules may be in hardware or software or combinations of hardware and software. In one embodiment, the computing device includes a microprocessor and a memory device coupled to the microprocessor, and the modules include software programs stored as program instructions in a computer readable medium associated with the memory device.

BRIEF DESCRIPTION OF THE DRAWINGS

FIG. 9A is a flowchart illustrating process steps for identifying skin pixels in the digital images according to one embodiment of the present invention.

FIG. 9B is a table listing ranges of pixels values for different color channels for each of a plurality of color spaces that are used to identify skin pixels.

FIG. 13B is a table listing pixel color and intensity associated with different skin conditions.

DETAILED DESCRIPTION

Figure 1:
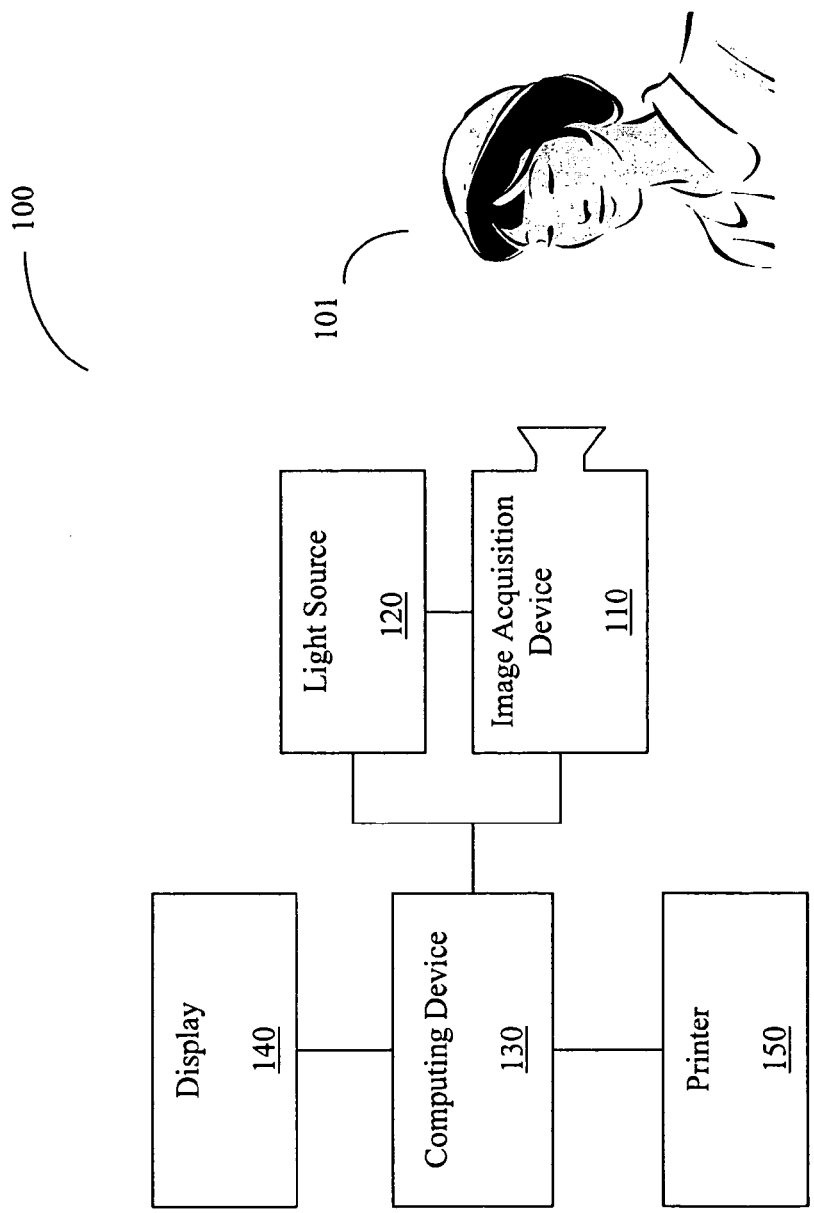
FIG. 1 is a simplified block diagram of a system for analyzing skin conditions according to embodiments of the present invention.

FIG. 1 depicts a simplified block diagram of a system 100 for analyzing skin conditions according to an embodiment of the present invention. As shown in FIG. 1, system 100 includes an image acquisition device 110, at least one light source 120 coupled to the image acquisition device 110, a computing device 130 coupled to the image acquisition device 110 and to the at least one light source either directly or through the image acquisition device 110, a display 140 coupled to the computing device 130, and optionally a printer 150 also couple to the computing device. System 100 is configured to acquire digital images of a subject 101, such as a person's face, and to process the digital images to obtain results related to at least one skin condition associated with the person.

Figure 2A:
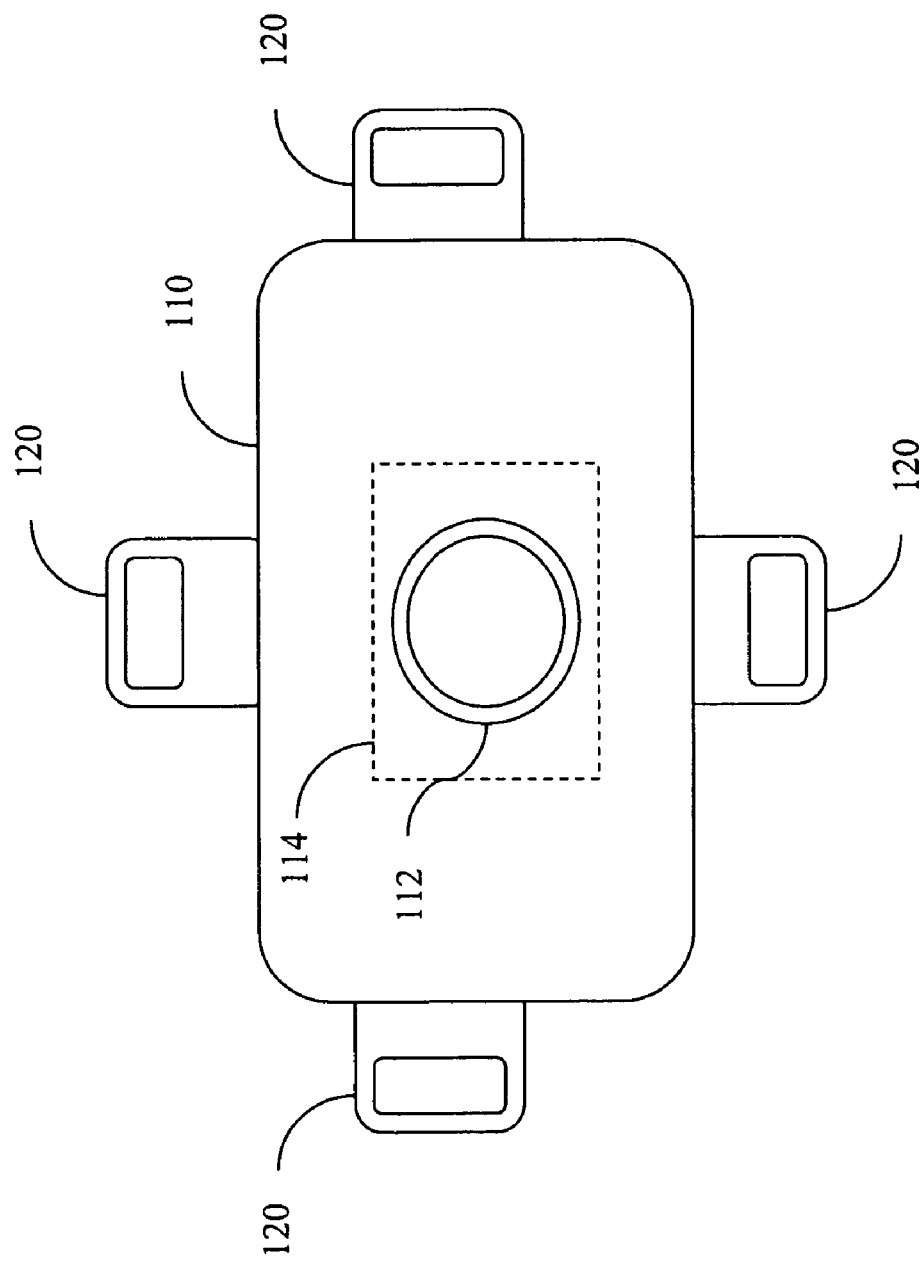
FIG. 2A is a line drawing of an image acquisition device in the system shown in FIG. 1 according to one embodiment of the present invention.
Figure 2B:
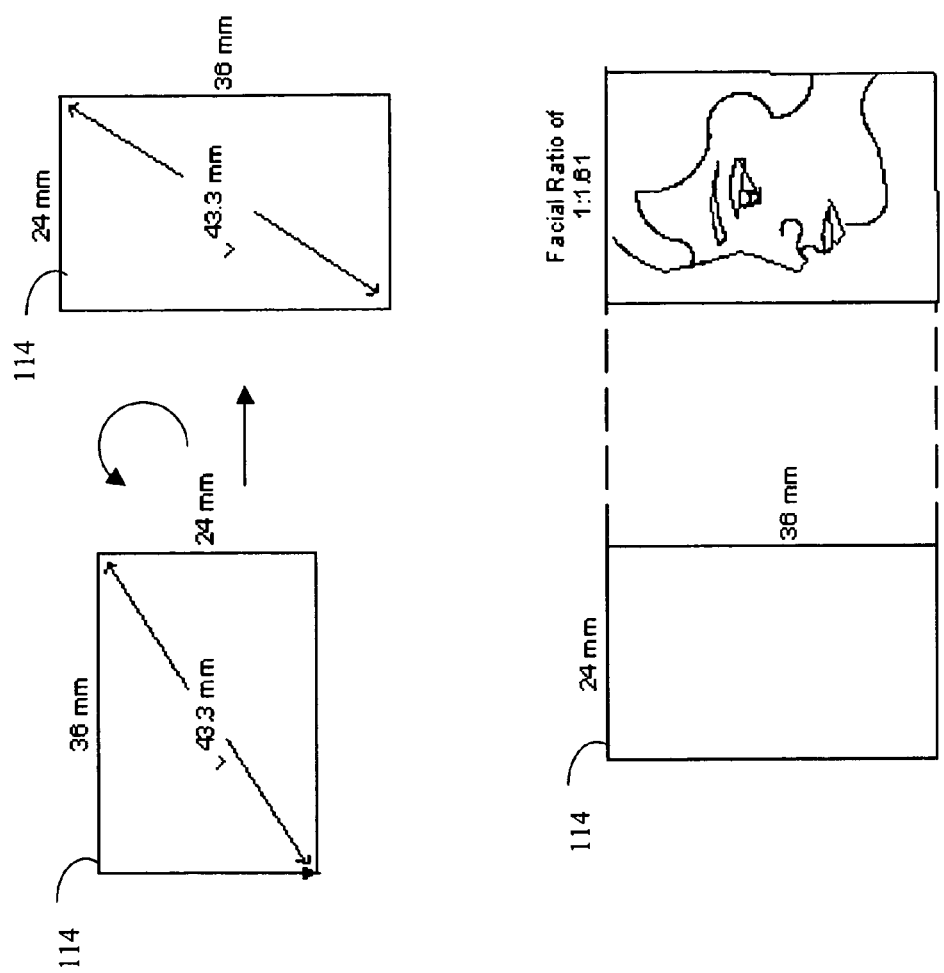
FIG. 2B is a line drawing showing an aspect ratio of a sensor in the image acquisition device being adjusted to accommodate the dimensions of a portion of a person's body surface to be imaged.

In one embodiment, as shown in FIG. 2, the image acquisition device 110 is part of a digital camera 200 having an image sensor 112 and an optical assembly 114 in front of the image sensor 112 and configured to form an image of the subject 101 on the image sensor 114. The image sensor 114 may include, for example, 3-5 millions of pixels made of photon detecting devices, such as charge-coupled devices (CCD). Each pixel includes three subpixels corresponding to three different color channels. In one embodiment, the image sensor 114 can be rotated to allow adjustment of its aspect ratio. As shown in FIG. 2B, the image sensor 114 is rotated to have its aspect ratio changed from 1.5:1 (36:24) to 1:1.5 (24:36) in order to capture the whole length of a person's face and to more accurately match a facial ratio of 1:1.61. In a further embodiment, the image sensor 114 has a variable number of pixels.

FIG. 2A also shows a plurality of light sources 120 as parts of the digital camera 200, including, for example, two flash light sources 120 on two sides of the camera, a flash light source 120 on top of the camera, and optionally another flash light source 120 at the bottom of the camera. Having more than one flash light sources 120 allows more uniform exposure of the subject 101 to light during imaging and to allow different light sources to be configured to emit different colors or wavelengths of light, but the number of light sources 120 and their positions in system 100 can be varied without affecting the general performance of the system. In one embodiment, a portion of the light sources 120 are configured to illuminate the subject 101 with white light, and another portion of the light sources 120 are configured to emit ultraviolet (UV) light.

Digital camera 200 may also include other parts or components that are not shown, such as a shutter, electronics for allowing the computing device 130 to control the shutter and the light sources 120, and electronics for outputting captured digital images to the computing device 130 for analysis, etc. To prevent saturation of the pixels in the image sensor 114, camera 200 may also include anti-blooming devices.

Figure 2C:
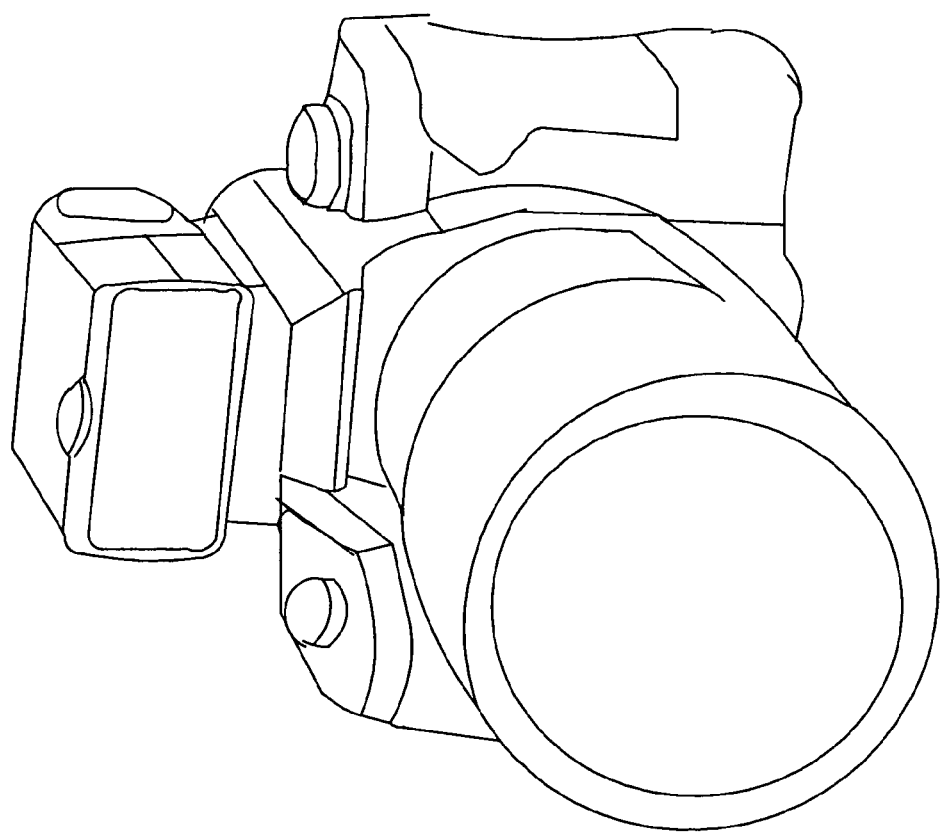
FIG. 2C is a line drawing of a three-dimensional view of a conventional image acquisition device that may be converted into the image acquisition device shown in FIG. 2A.
Figure 3:
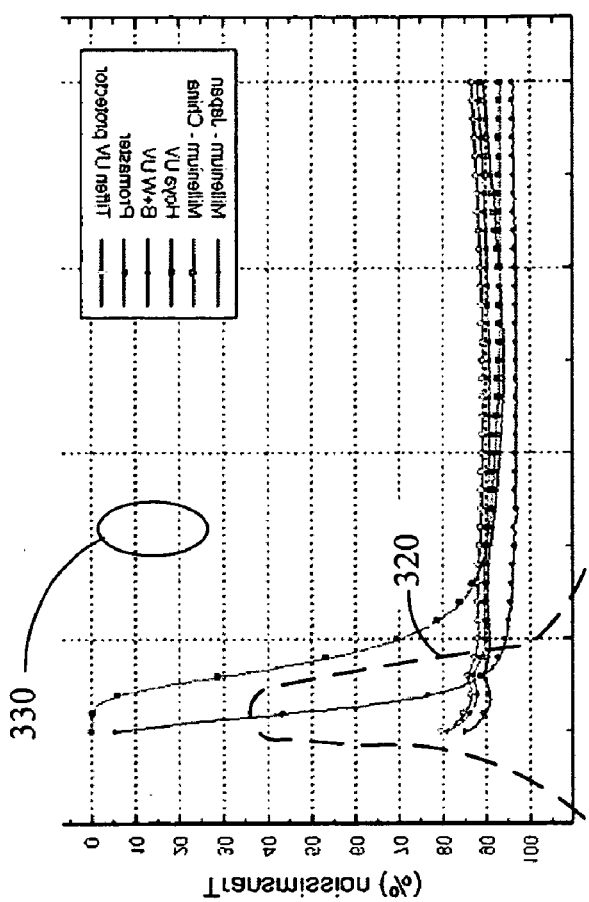
FIG. 3A is a line drawing of a flash light source in the system shown in FIG. 1 according to one embodiment of the present invention.
FIG. 3B is a chart illustrating a transmission spectrum of a UV bandpass filter as compared with transmission spectra of other white-light filters.
Figure 3:
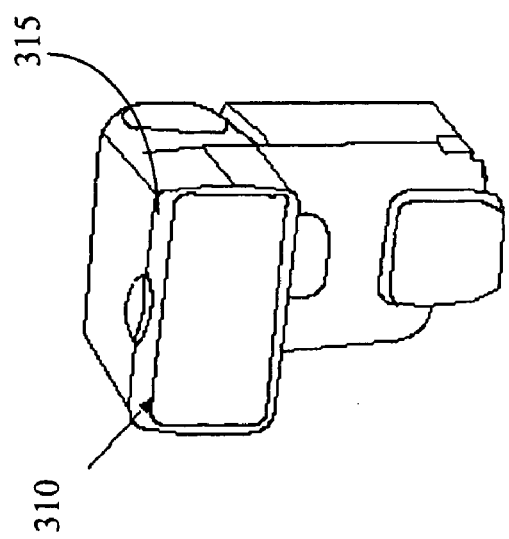

In one embodiment, camera 200 is converted from a conventional, off-the-shelf digital camera, such as the one shown in FIG. 2C, by adding the light sources 120 on the sides and the bottom, and electronic and mechanical components to allow sensor 114 to rotate as directed. In one embodiment, the light sources 120 that are on the top and at the bottom of the camera 200 are white light sources and the light sources 120 on the sides are UV light sources. The white light sources can be conventional off-the-shelf flash light sources, such as the flash light source 300 shown in FIG. 3. Each of the UV light sources 120 can be one converted from light source 300 by changing a low-pass filter 310 in front of the light source 300 into a UV filter 310. In one embodiment, as shown in FIG. 3B, the UV filter is a bandpass filter that provides a transmission spectrum 320 having a width of about 50 nm and a peak wavelength of about 365 nm. In comparison, the low-pass filter 310 would provide a transmission spectrum, such as one of spectra 330 shown in FIG. 3B, that drop sharply to near zero in the UV wavelength range and stay relatively flat in the visible wavelength range. In addition to the white-light and UV filters, some or all of the light sources 120 may also have infrared absorbing filters 315 installed. The infrared absorbing filters help to prevent heat from the light source to be applied to the subject by filtering out wavelengths greater than, for example, 700 nm.

Figure 4:
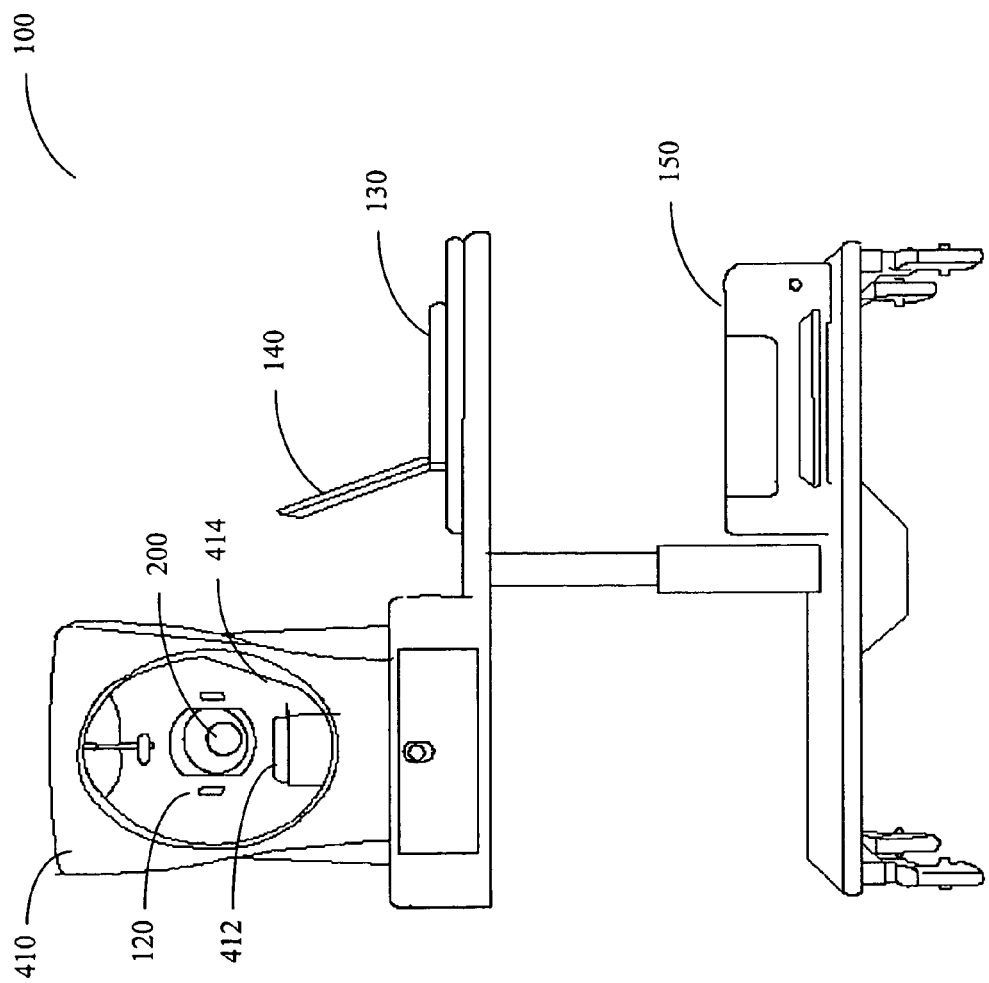
FIG. 4 is a line drawing of a setup for the system illustrated in FIG. 1 according to according to one embodiment of the present invention.

Camera 200 may be installed in or next to an imaging box, such as box 410 shown in FIG. 4, which illustrates a setup of the system 100. Imaging box 410 helps to prevent ambient light from entering the sensor 212 of the camera and interfering with the analysis of skin conditions. An example of such an imaging box is the Facial Stage DM-3 commercially available from Moritex in Japan. FIG. 4 also shows camera 200 placed near a center in the back of the box 410, light sources 120 on top and sides of the optical assembly 214, and a pedestal or chin rest 412 near an opening 414 of the imaging box help the subject 101 to stay still during imaging. FIG. 4 also shows, as an example, the computing device 130 and the display 140 as parts of a laptop computer and a printer 150 placed under the laptop computer.

Figure 5:
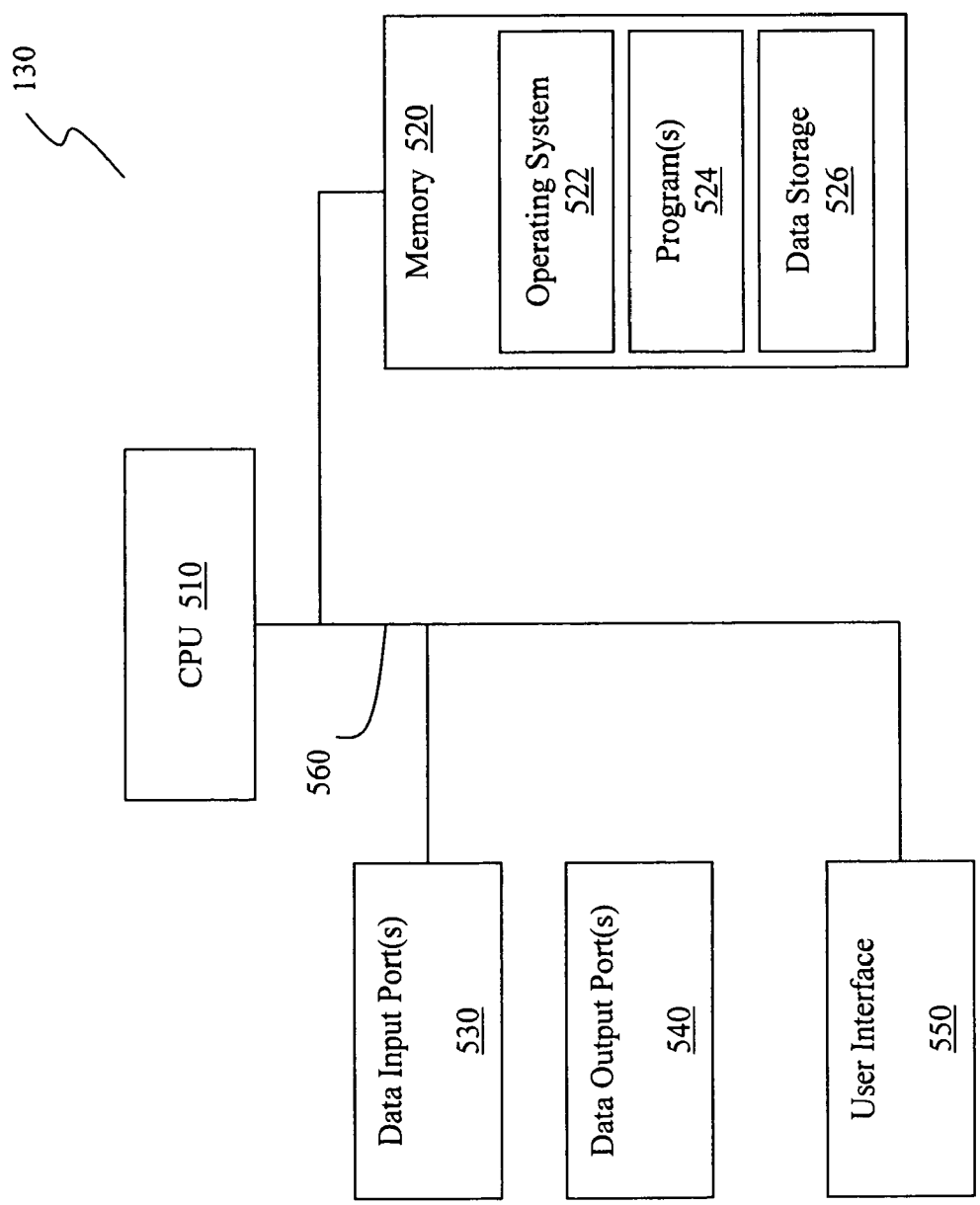
FIG. 5 is a simplified block diagram of a computing device in the system illustrated in FIG. 1 according to one embodiment of the present invention.

In one embodiment of the present invention, as shown in FIG. 5, the computing device 130 can be any computing device having a central processing unit (CPU) 510, a memory unit 520, at least one data input port 530, at least one data output port 540, and a user interface 550, interconnected by one or more buses 560. Memory unit 520 preferably stores operating system software 522 and other software programs including a program 524 for analyzing skin conditions using digital images. Memory unit 520 further includes a data storage unit 526 for storing image data transferred from the camera 200 through one of the at least one data input port 530 and for storing prior skin condition results associated with the subject and other data or data structures generated during current execution of the programs 524, as discussed below. Programs 524 may be organized into modules each includes coded instructions, which, when executed by the CPU 510, cause the computing device 130 to carry out different aspects, modules, or steps of a method for analyzing skin conditions using digital images, according to one embodiment of the present invention, as described in more detail below. All of part of the memory unit 520, such as the database 526, may reside in a different geographical location from that of the CPU and be coupled to the CPU through one or more computer networks.

Figure 6:
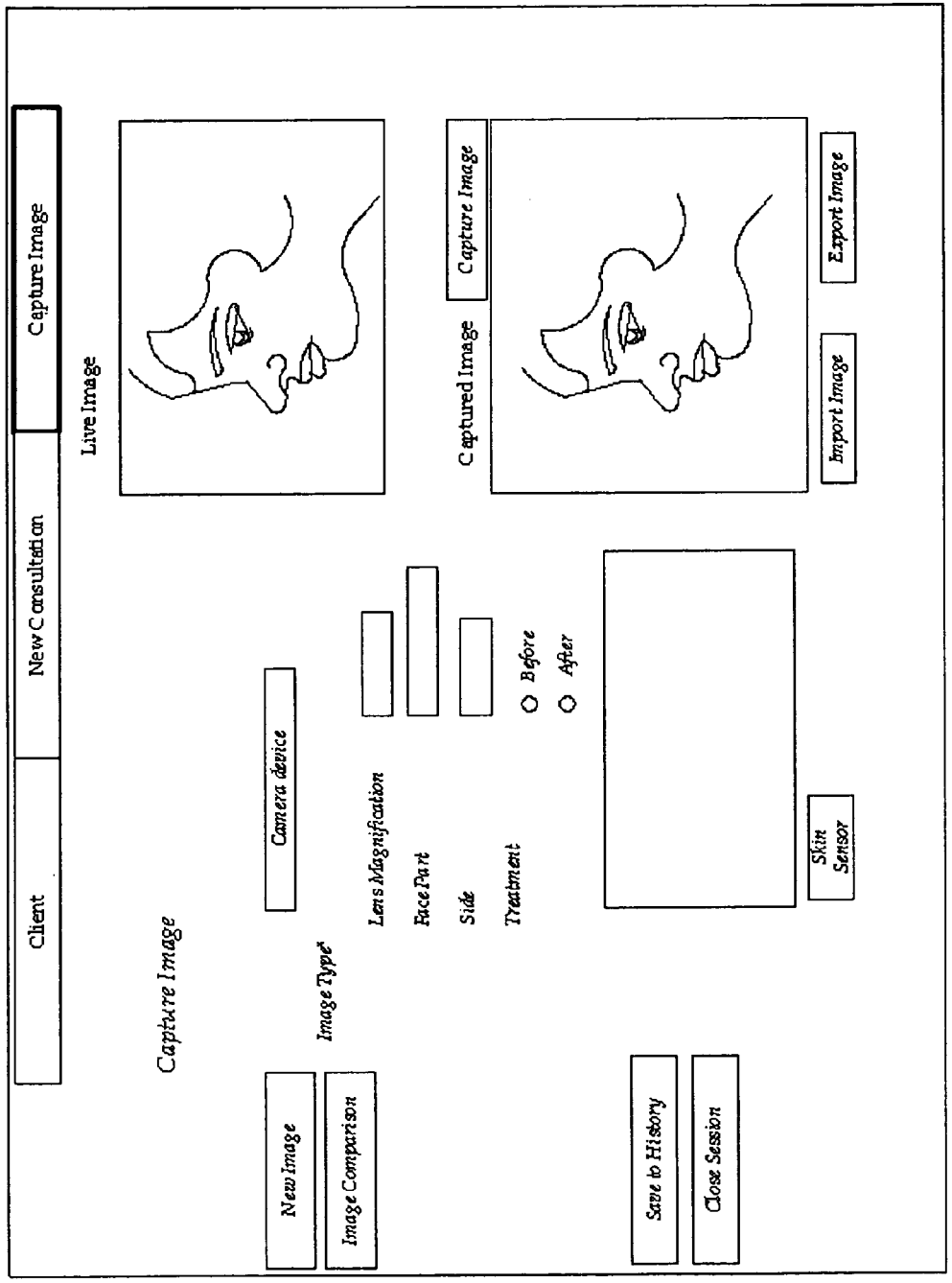
FIG. 6 is a line drawing of a user interface associated with the computing device according to one embodiment of the present invention.

Programs 524 may also include a module including coded instructions, which, when executed by the CPU 510, cause the computing device 130 to provide graphical user interfaces (GUI) for a user to interact with the computing device 130 and direct the flow of the programs 524. An example of a GUI for capturing digital images of the subject 101 is illustrated in FIG. 6.

Figure 7:
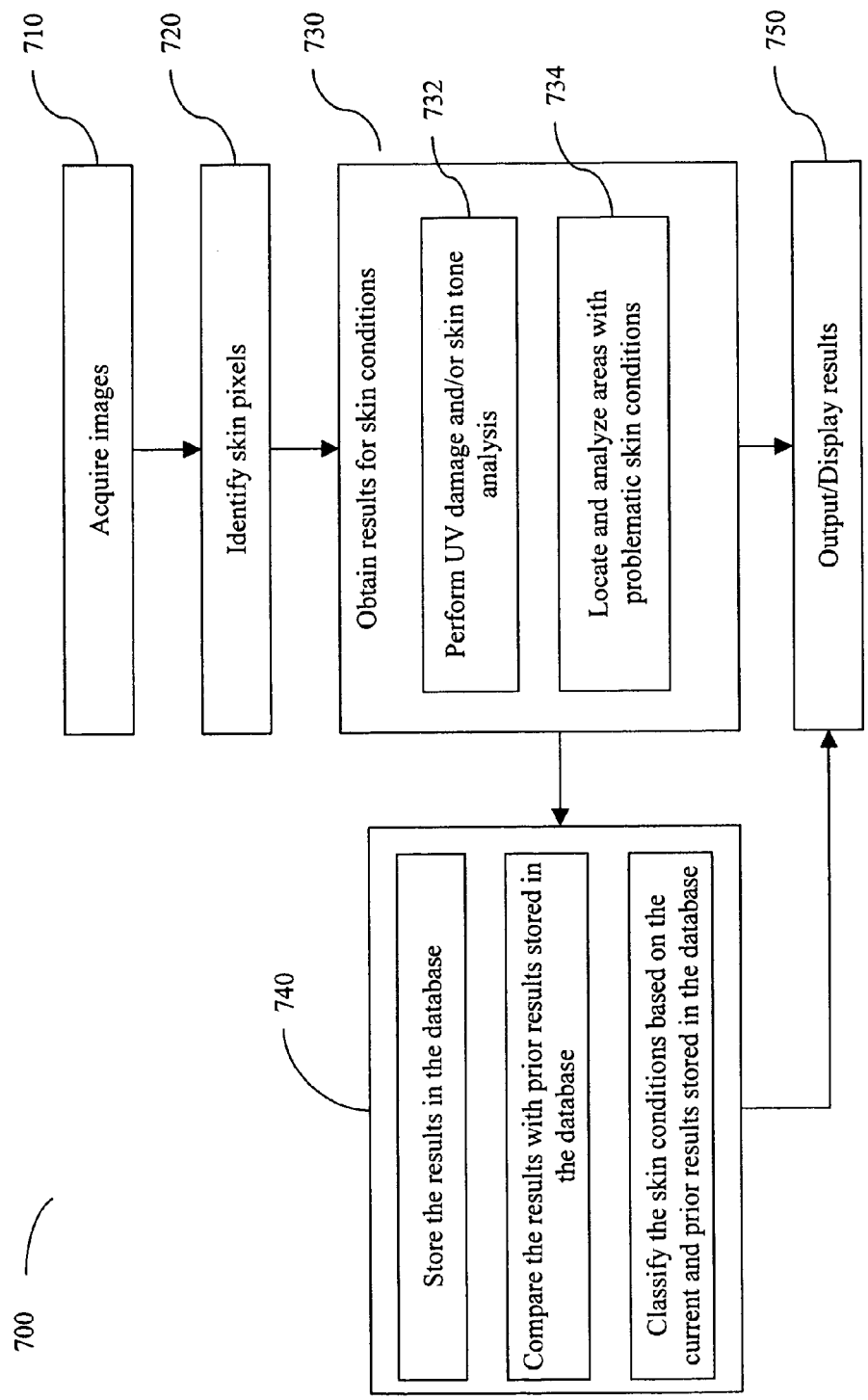
FIG. 7 is a flowchart illustrating a method for analyzing skin conditions using digital images according to one embodiment of the present invention.

FIG. 7 is a flowchart illustrating a method 700 for analyzing skin conditions using digital images according to one embodiment of the present invention. As shown in FIG. 7, method 700 includes a module 710 for acquiring digital images of the subject 101. In one embodiment, the acquired digital images include a first white-light image and a first UV image. Each of the first white-light and UV images includes a plurality of pixels. Each pixel in the first white-light or UV image corresponds to a pixel in the sensor 114. In one embodiment, each of the pixels in the sensor 114 includes three subpixels corresponding to three color channels for sensing three color components in a received light signal. Thus, each pixel in the white-light and UV image includes values associated with the three color channels, which are referred to sometimes in this document as pixel values. The pixel values may range, for example, between 0 and 255.

The images captured by the sensor 114 and the images used by the computing device 130 may be of different formats. An appropriate image conversion software may be used by the computing device 130 to convert an image format, such as BMP, TIFF, or FITS, used by the camera 200 to another image format used by the computing device 130. The images from the camera, after any conversion, may be initially processed by the computing device 130 using conventional techniques for dark current and/or intensity correction, and image manipulation or enhancement, before being used for analyzing skin conditions. The images may also be initially processed to have some pixels, such as those at the four corners of a rectangular image, taken out because it may be easy to tell that they have collected information from surrounding objects, instead of from the subject 101. Thus, each of the acquired digital images, such as the first white-light and UV images, is referred to as either the original image acquired by the camera or an image derived from the original image after one or more format or color space conversions, and/or after some initial processing such as those stated above.

Generally, the subject 101, or part of it, that is captured in the images include both skin and non-skin portions or features, such as hair, clothing, eyes, lips, nostrils, etc. Furthermore, some of the objects surrounding the subject 101 may also be captured in the images. Therefore, the pixels in the first white-light and UV images often include both skin pixels, meaning pixels that have captured signals from the skin portions of the subject 101, and non-skin pixels, meaning pixels that have captured signals from non-skin features of the subject 101 or from objects surrounding the subject 101.

Since non-skin pixels may interfere with the analysis of skin conditions, method 700 further includes a module 720 for identifying, on a pixel by pixel basis, skin pixels and/or non-skin pixels in the first white-light and/or UV image, and a module 730 for obtaining results associated with at least one skin condition using only information in the skin pixels in the first white light and UV images. Module 730 may include submodules 732 for performing UV damage and skin tone analysis, and submodules 734 for locating and quantifying localized skin conditions, such as one or more types of pores, wrinkles, moles, pigmentation, melanoma, etc. Module 730 may also include submodules (not shown) for examining other skin conditions, such as hydration levels, collagen content, and skin type, moles, pigmentation, level of oil flow, and/or any or the other skin conditions identifiable using the information in one or both of the white-light and UV images according to knowledge known to those familiar with the art.

Method 700 further includes a module 740 in which module 700 interact with the database 526 to store the current results in the database, compare the current results with prior results associated with the same subject 101, and/or to classify the skin conditions based on the comparison. Method 700 further includes a module 750 for outputting and/or displaying results from the analysis.

Figure 8A:
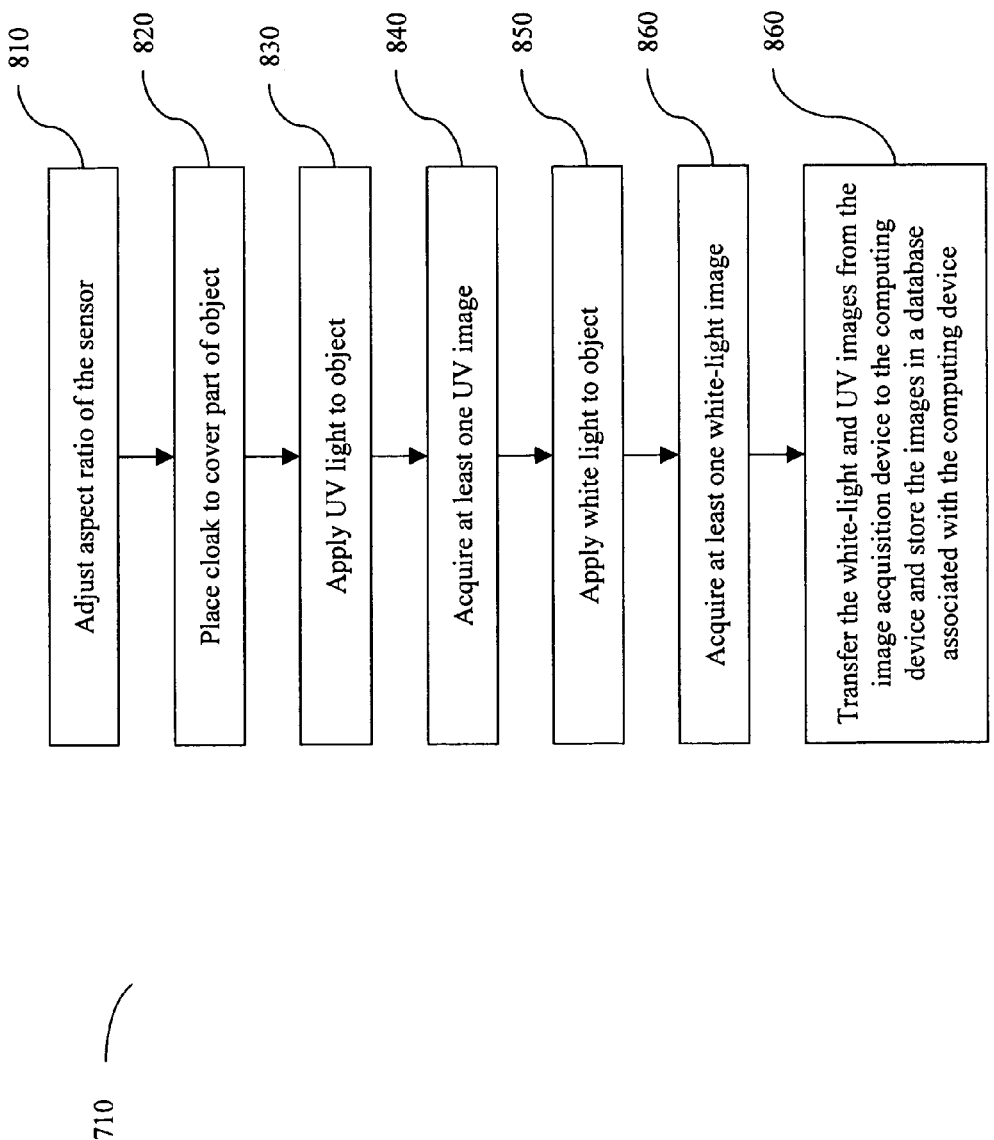
FIG. 8A is a flowchart illustrating process steps for acquiring digital images of a body surface according to one embodiment of the present invention.
Figure 8B:
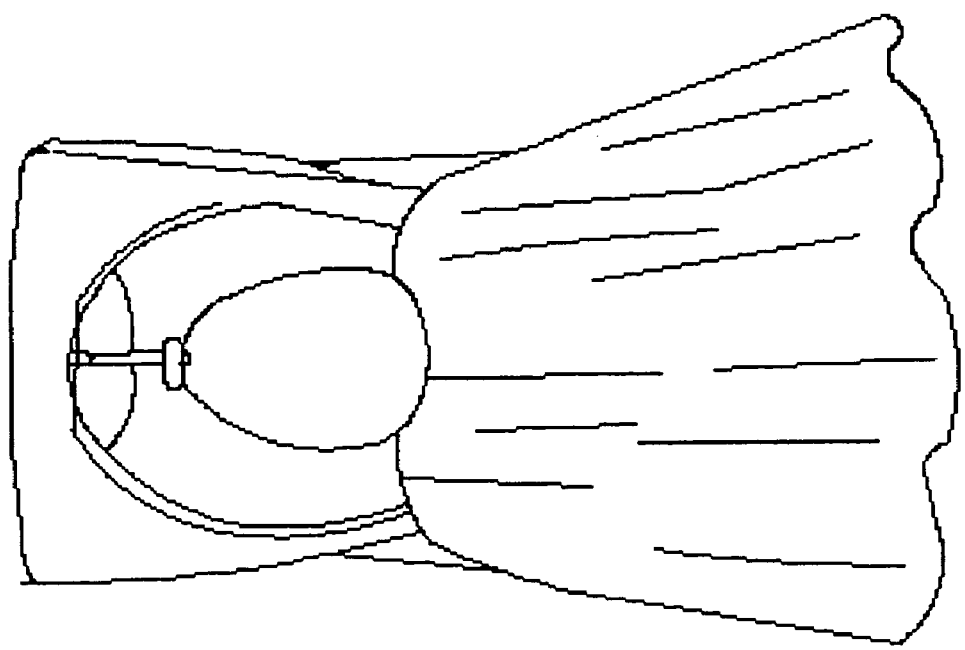
FIG. 8B is a line drawing of a person in front of an image acquisition device and having a cloak placed thereon according to according to one embodiment of the present invention.

FIG. 8A illustrates process steps in the module 710 for acquiring the digital images of the subject 101 according to one embodiment of the present invention. As shown in FIG. 8A, module 710 includes a step 810 in which the aspect ratio of the sensor 114 is adjusted according to dimensions of the subject 101, and a step 820 in which a light absorbing cloak is placed over the subject 101 to cover as much as possible non-skin portions of the subject 101. For example, as illustrated in FIG. 8B, a person in front of the box 410 to have his or her face imaged by the camera 200 may have his or her shoulders and chest covered by a cloak 880 such that the person's clothing would not be captured by the camera and that the subject is allowed to reach full fluorescence under UV illumination. In one embodiment, the cloak 880 is made of one or more layers of light absorbing fabric such as one known as Tuf-Flock or Tough Lock, which is a vinyl backed velour that can be purchased at photography specialty stores.

Module 710 further includes a step 830 in which the UV light sources 120 are turned on to send a flash of UV light to the subject 101. The flash of UV light should include a band of UV wavelengths the can causes the skin associated with the subject 101 to fluoresce, as illustrated in FIG. 3B. At about the same time, the shutter of the camera is opened at step 840 so that the first UV image is captured by the sensor 114.

The application of ultraviolet (UV) light to dermatology and health care has been researched and utilized in order to aid in the detection and diagnosis of a number of afflictions or skin disorders. Given that most living organisms fluoresce upon excitation through the absorption of light, a phenomenon known as autofluorescence, it has been shown that different organisms can be classified through their Stokes shift values. Stokes shift is the difference between peak wavelength or frequency of an absorption spectrum and peak wavelength or frequency of an emission spectrum. Furthermore, UV light can penetrate deeper into the skin than visible light, making it possible to detect subsurface skin conditions (i.e., skin conditions below the surface) and allowing for early diagnosis of melanoma and other skin cancer symptoms. Therefore, by acquiring the first UV image, the embodiments of the present invention is able to combine the knowledge of autofluorescence of the skin and image processing technologies to provide automated detection and analysis of subsurface skin condition, as described in more detail below.

Module 710 further includes a step 850 in which the white light sources 120 are turned on to send a flash of white light to the subject 101. The flash of white light preferably has wavelengths that span across a full spectrum of visible light or a substantial portion of it. At about the same time, the shutter of the camera is opened at step 860 so that the first white-light image is captured by the sensor 114. Module 710 further includes a step 870 in which the first white-light and UV images are transferred from the camera 200 into the computing device 130 using conventional means and stored in database 526 for subsequent processing, and in which appropriate image conversion and/or initial processing are performing as discussed above.

In module 720, skin pixels in the first white-light and UV images are identified by examining each pixel in the first white-light and/or UV image to determine if properties of the pixel satisfy predefined criteria for skin pixels, according to one embodiment of the present invention. The properties of a pixel may include the pixel values, the pixel's position in the image, pixel values of one or more corresponding pixels in one or more other images (as discussed below), and/or its relationship with a skin map or skin mask. As shown in FIG. 9A, module 720 includes a step 810 in which each pixel in the white-light image is examined to determine if the pixel values associated therewith satisfy a first set of predefined criteria for skin pixels. The criteria for skin pixels may be different for different color spaces, as illustrated in FIG. 9B, which lists, for each of a plurality of color spaces, ranges of values associated with different color channels for likely skin pixels.

For example, assuming the first white-light image being in a first color space, such as the red-green-blue (RGB) color space, pixels that have the red channel (channel 1) values in the range of 105-255, the green channel (channel 2) values in the range of 52-191, and the blue channel (channel 3) values in the range of 32-180 are likely to be skin pixels. Thus, as shown in FIG. 10(a), after examining the pixels in the first white-light image 1010, part of the pixels in the first white-light image 1010 are considered to be likely skin pixels, as illustrated by the white blocks in FIG. 10(a), and the rest of the pixels in the first white-light image 1010 are determined to be non-skin pixels, as illustrated by the black blocks in FIG. 10(a).

To be more accurate in identifying the skin pixels, module 720 further includes a step 820 in which the first white light image 1010 is converted to at least one other white light images in at least one other color space, such as white-light image 1020 in a second color space illustrated in FIG. 10(b), and white-light image 1030 in a third color space illustrated in FIG. 10(c). Each pixel in the at least one other white-light image corresponds to a respective pixel in the first white-light image. The first, second, and third color spaces can be different ones selected from commonly known color spaces, such as the RGB, YIQ, LAB, YcBcR, and HSV color spaces, and/or any proprietary color spaces.

Module 720 further includes step 830 in which, for each of the at least one other white light images, the pixels corresponding to the likely skin pixels in the first white-light image 1010 are further examined against criteria for skin pixels associated with the respective color space. For example, in the second white-light image 1020, all pixels corresponding to non-skin pixels in the first white-light image 1010 are deemed to be non-skin pixels and are illustrated in FIG. 10(b) as black blocks, and pixels corresponding to likely skin pixels in the first white-light image 1010 are further examined against criteria for skin pixels associated with the second color space. As a result, more pixels would be determined as non-skin pixels, which are shown in FIG. 10(b) as blocks with stripes. The rest of the pixels in the second white-light image 1020 are considered to be likely skin pixels and are illustrated by the white blocks in FIG. 10(b).

Furthermore, in the third white-light image 1030, all pixels corresponding to non-skin pixels in the second white-light image 1020 are deemed to be non-skin pixels and are illustrated in FIG. 10(c) as black blocks and blocks with stripes, and pixels corresponding to likely skin pixels in the second white-light image 1020 are further examined against criteria for skin pixels associated with the third color space. As a result, more pixels would be determined as non-skin pixels, which are shown in FIG. 10(c) as blocks with dots. The rest of the pixels in the third white-light image 1020 are considered to be likely skin pixels and are illustrated by the white blocks in FIG. 10(c). This process may continue until a last one of the at least one other white-light image (the last white-light image) is examined.

Figure 10:
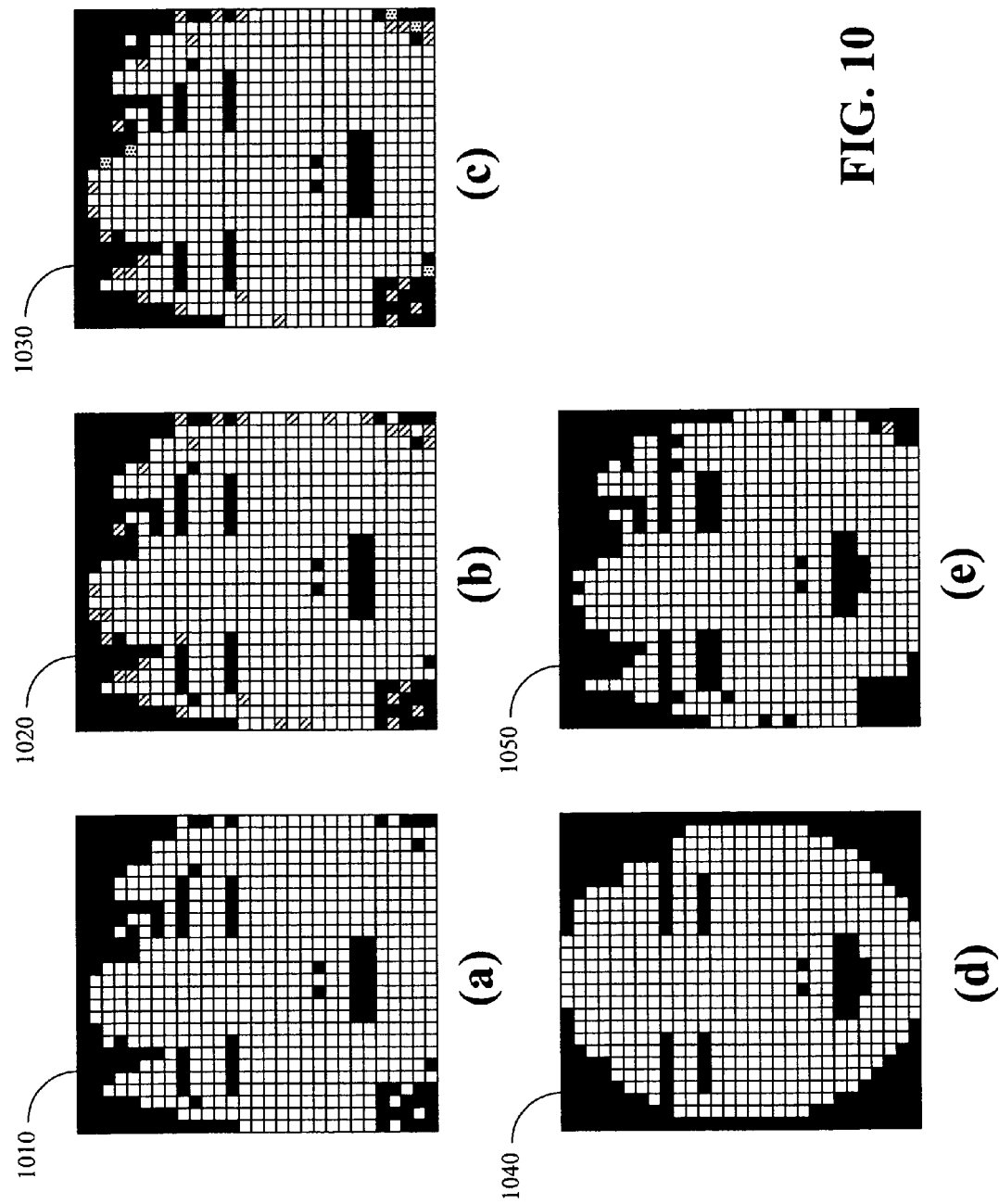
FIGS. 10(a) to 10(e) are simplified block diagrams illustrating a method for generating a skin mask according to one embodiment of the present invention.

To be even more accurate in identifying the skin pixels and to make sure that non-skin pixels are not considered in analyzing the skin conditions, module 720 may include a further step 840 in which a coordinate reference 1040, such as the one shown in FIG. 10(*d*) is used to classify more of the likely skin pixels as non-skin pixels. The coordinate reference 1040 may be pre-stored template together with a plurality of other coordinate reference or templates in the database 526 in memory unit 520 of the computing device 130, and selected as being a suitable one for the subject 101. The coordinate reference defines certain pixels in any of the white-light images as non-skin pixels (shown as black blocks in FIG. 10(*d*)) based on their coordinates or positions in the image. So if any of the likely skin pixels in the last white-light image have coordinates that are defined as coordinates for non-skin features in the coordinate reference 1040, these pixels are determined to be non-skin pixels. The rest of the like skin pixels in the last white-light image are finally identified as skin pixels, and all of the pixels in each of the other white-light images or the UV image that correspond to the skin pixels in the last white-light image are also identified as skin pixels. The rest of the pixels in each of the white-light or UV images are considered as non-skin pixels.

To help identify skin pixels in all of the images of the subject 101 during subsequent processing, module 720 may include a further step 850 in which a skin map or skin mask is generated. In one embodiment of the present invention, as shown in FIG. 10(*e*), the skin map 1050 includes a matrix or data group having a plurality of elements, each corresponding to a pixel in any of the white-light or UV images of the subject 101. Those matrix elements corresponding to skin pixels in the last white-light image (shown as white blocks in FIG. 10(*e*)) are defined as skin elements, and each is assigned a first value. In contract, those matrix elements corresponding to non-skin-pixels in the last white-light image (shown as black blocks in FIG. 10(*e*)) are defined as non-skin elements, and each is assigned a second value that is distinct from the first value. In one embodiment, the first value is a large number, such as 255, and the second value is a small number, such as 0. Thus, whether a pixel in any of the white-light and UV images is a skin pixel can be easily determined by looking up the value contained in the corresponding element in the skin map 1050, and this can be done in step 850.

Figure 11:
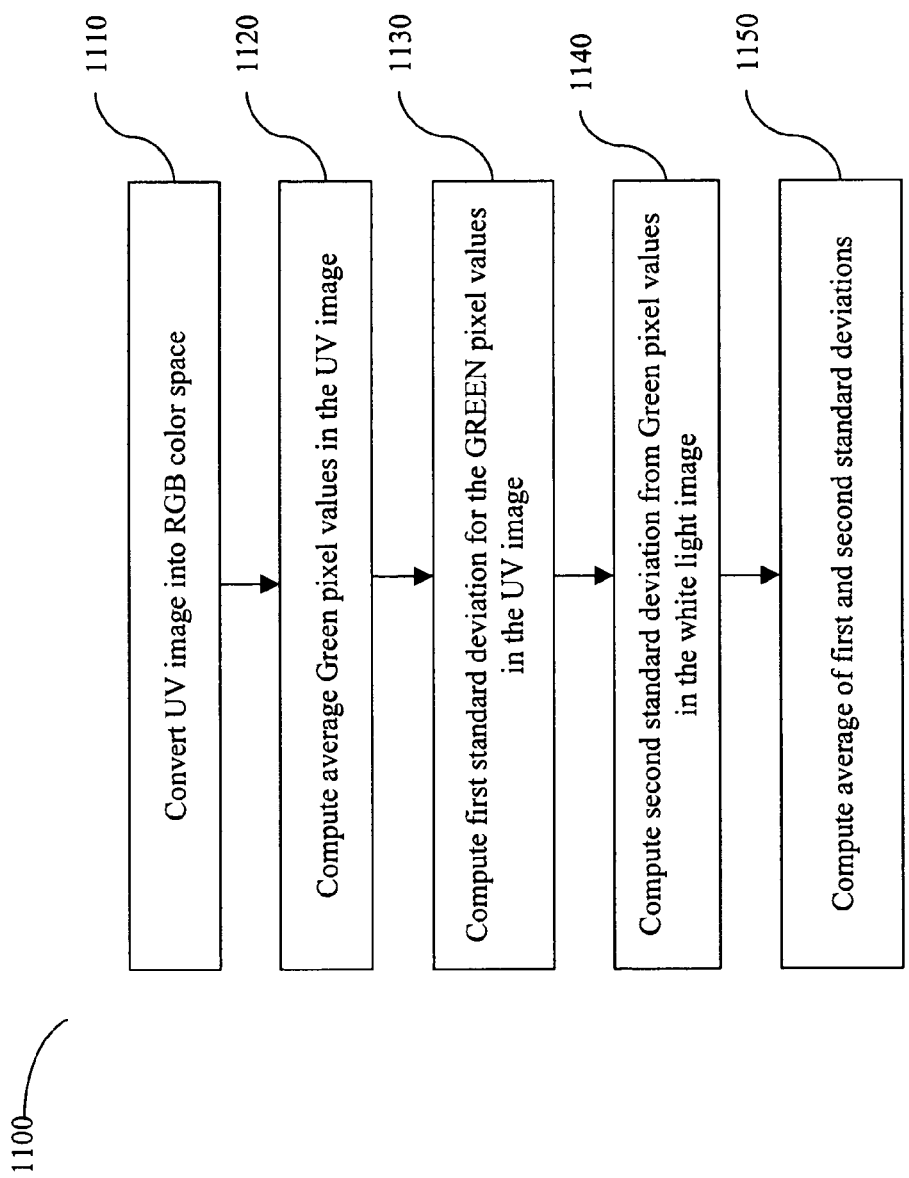
FIG. 11 is a flowchart illustrating process steps for obtaining UV damage results from the digital images according to one embodiment of the present invention.

In one embodiment of the present invention, module 730 include a submodule 1100 for obtaining UV damage results using the skin pixels in at least the first UV image, as illustrated in FIG. 11. Submodule 1100 includes a step 1110 in which the first UV image, if it is not in the RGB color space, is converted into the RGB color space, a step 1120 in which an average is computed from all of the Green channel values in the skin pixels of the first UV image, and a step 1130 in which a first standard deviation is computed from the Green channel values in the skin pixels. The first standard deviation value can be used to indicate quantitatively the amount of UV damage in the skin of the subject 101. Alternatively or additionally, submodule 1100 may include a further step 1140 in which a second standard deviation is computed from the Green channel values in the skin pixels of one of the white-light image, and an average of the first and second standard deviation values can be used to indicate quantitatively the amount of UV damage in the skin of the subject 101.

In order to visually display the UV damage in an enhanced view, a UV damage enhanced white light image is formed in step 1150 that has a plurality of pixels each corresponding to a respective pixel in the first white-light image. Thus, a non-skin pixel in the first white-light image corresponds to a non-skin pixel in the UV damage enhanced white-light image. In one embodiment, the non-skin pixels in the UV damage enhanced white-light image have the same pixel values as the pixel values in the non-skin pixels in the first white-light image. For each skin-pixel in the UV damage enhanced white-light image, the red-channel and blue-channel values therein are the same as those in the corresponding skin pixel in the first white-light image, but the green channel value therein is derived from both the green channel value in the corresponding skin pixel in the first white-light image and the green channel value in the corresponding pixel in the first or second UV image. For example, assuming $G_{EN}$ is the green channel value in a skin pixel in the UV damage enhanced white-light image, and $G_{WL}$ and $G_{UV}$ are the green channel value in the corresponding skin pixels in the first white-light and the first (or second) UV images, respectively, $G_{EN}$ may be assigned to be an average of $G_{WL}$ and $G_{UV}$, or $G_{EN}=\frac{1}{2}(G_{WL}+G_{UV})$. Other ways of enhancing the UV damages are also possible, for example, $G_{EN}=G_{WL}+(G_{UV}-G_{AVG})$, where $G_{AVG}$ is the average green channel value computed in step 1120.

Figure 12:
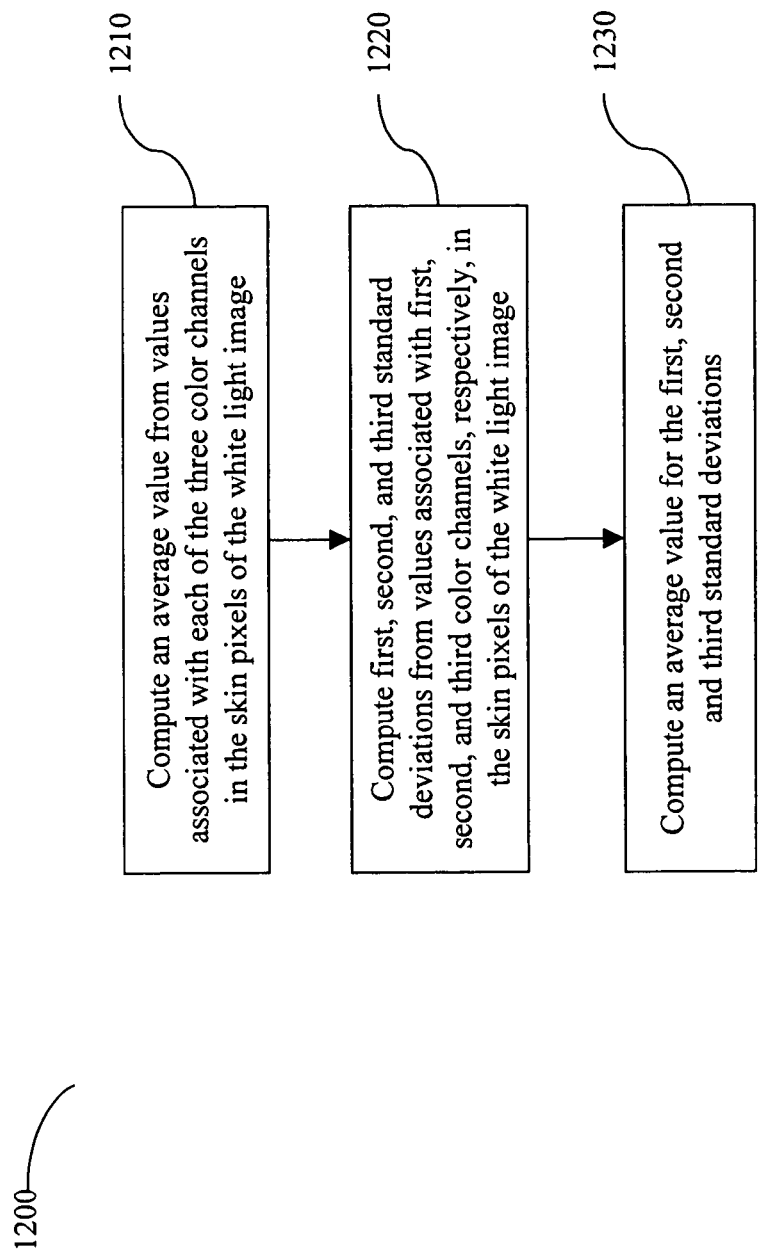
FIG. 12 is a flowchart illustrating process steps for obtaining skin tone results from the digital images according to one embodiment of the present invention.

In one embodiment of the present invention, module 730 includes a submodule 1200 for obtaining skin tone results using the skin pixels in any of the white light image, as illustrated in FIG. 12. Submodule 1200 includes a step 1210 in which an average is computed from values associated with each of the three color channels in the skin pixels of the white-light image, a step 1220 in which a standard deviation is computed for each of the color channels in the skin pixels, and a step 1230 in which an average of the standard deviation values computed in step 1220 is obtained as a measure of the skin tone of the subject 101.

Figure 13A:
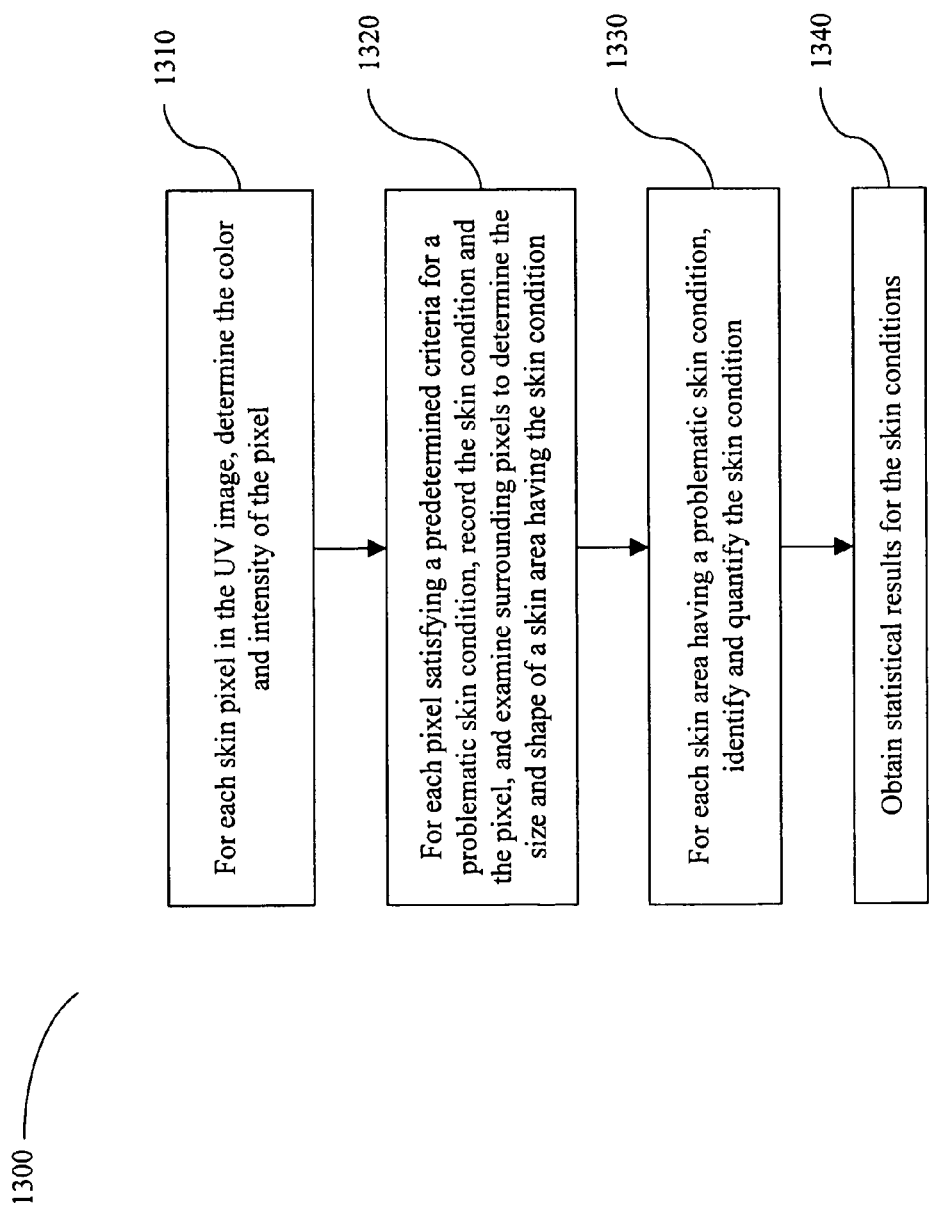
FIG. 13A is a flowchart illustrating process steps for obtaining results related to certain skin conditions according to one embodiment of the present invention.

In one embodiment of the present invention, module 730 includes a submodule 1300 for obtaining results related to certain skin conditions, as illustrated in FIG. 13A. Submodule 1300 includes a step 1310 in which color and intensity values are computed from the pixel values associated with each pixel in one of the UV images, and a step 1320 in which the color and intensity values for each pixel are examined with reference to at least one lookup table to determine if the pixel satisfy criteria for any of a list of skin conditions in the lookup table. The at least one lookup table may include those compiled using knowledge known in the art, or through proprietary research and/or empirical studies. For each skin pixel identified to be associated with a certain skin condition, the surrounding pixels are also examined to determine the size and shape of a skin area having the skin condition. In the case of melanoma, the shape and size of an affected skin area can be used to help determine the type and amount of skin cancer damage.

FIG. 13B illustrate an exemplary lookup table for pores and sluggish oil flow that may be included in the at least one lookup table. For example, if a first skin pixel has a white color and an intensity value exceeds 130, the skin pixel is likely one of a group of contiguous pixels that have captured fluorescence coming from an inflamed pore upon illumination by a UV flash. To confirm, surrounding skin pixels are also examined to see if some of them are also white in color and have intensity values over 130. If none or few of the pixels satisfy this criteria, the first skin pixel is not associated with an inflamed pore. Otherwise, an inflamed pore is identified, and in step 1330, the number of skin pixels associated with the inflamed pore is determined as a measure for the shape and size of the pore, and an average of the intensity value associated with the number of skin pixels is computed as a quantitative indication of the severity of the pore.

Note that FIG. 13B only illustrates some examples of the criteria that can be used by module 1300. Alternatively or additionally, module 1300 may use other lookup tables associated with other skin conditions, such as those known in the art.

Submodule 1300 further includes a step 1340 in which statistical results such as a total number of all types skin conditions, and/or a total number of each of a plurality of skin conditions are computed.

Figure 14:
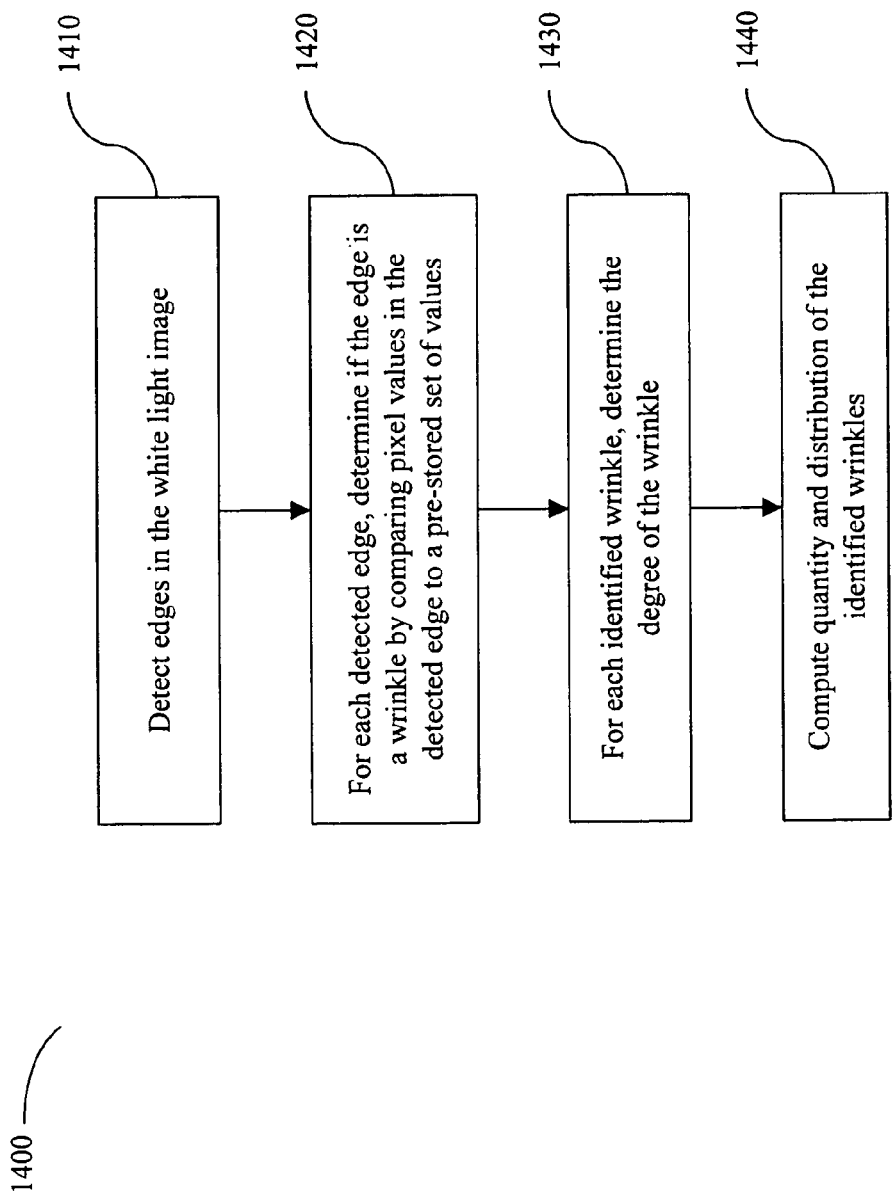
FIG. 14 is a flowchart illustrating process steps for obtaining results related to wrinkles according to one embodiment of the present invention.

In one embodiment of the present invention, module 730 further includes a submodule 1400 for evaluating wrinkles on the subject 101, as shown in FIG. 14. Submodule 1400 includes a step 1410 in which a conventional or proprietary edge detector, such as the publicly available Canny edge detector, is used to detect edges in any of the white-light image after the non-skin pixels are extracted from the white-light image, and a step 1420 in which each detected edge is examined to determine if it is a wrinkle. In one embodiment, an edge is determined to be a wrinkle if a predetermined percentage of corresponding pixels have pixel values satisfy predetermined criteria. In one embodiment, the predetermined criteria are derived from prestored or recently computed skin color values for the subject. For example, average values for the red, green, and blue color channels for the subject can be used to set the criteria, and if a predetermined percentage, such as over 70% of the pixels corresponding to the edge have their red, green, and blue channel values roughly proportional to the average red, green blue channel values, the edge would be determined as a wrinkle.

Submodule 1400 may further include a step 1430 in which the pixels around the edges are examined to determine the degree of the wrinkle. For example, for a fine line wrinkle, the pixels corresponding to the edge indicating the likely presence of the wrinkle should have intensity values substantially less than those of the surrounding pixels, and for a deep wrinkle, a wider edge should be expected, and there should be a wider line of pixels having depressed intensity value.

Submodule 1400 may further include a step 1440 in which the number of all wrinkles or wrinkles of a certain degree is counted, and a distribution of the wrinkles across the subject may also be computed.

Figure 15A:
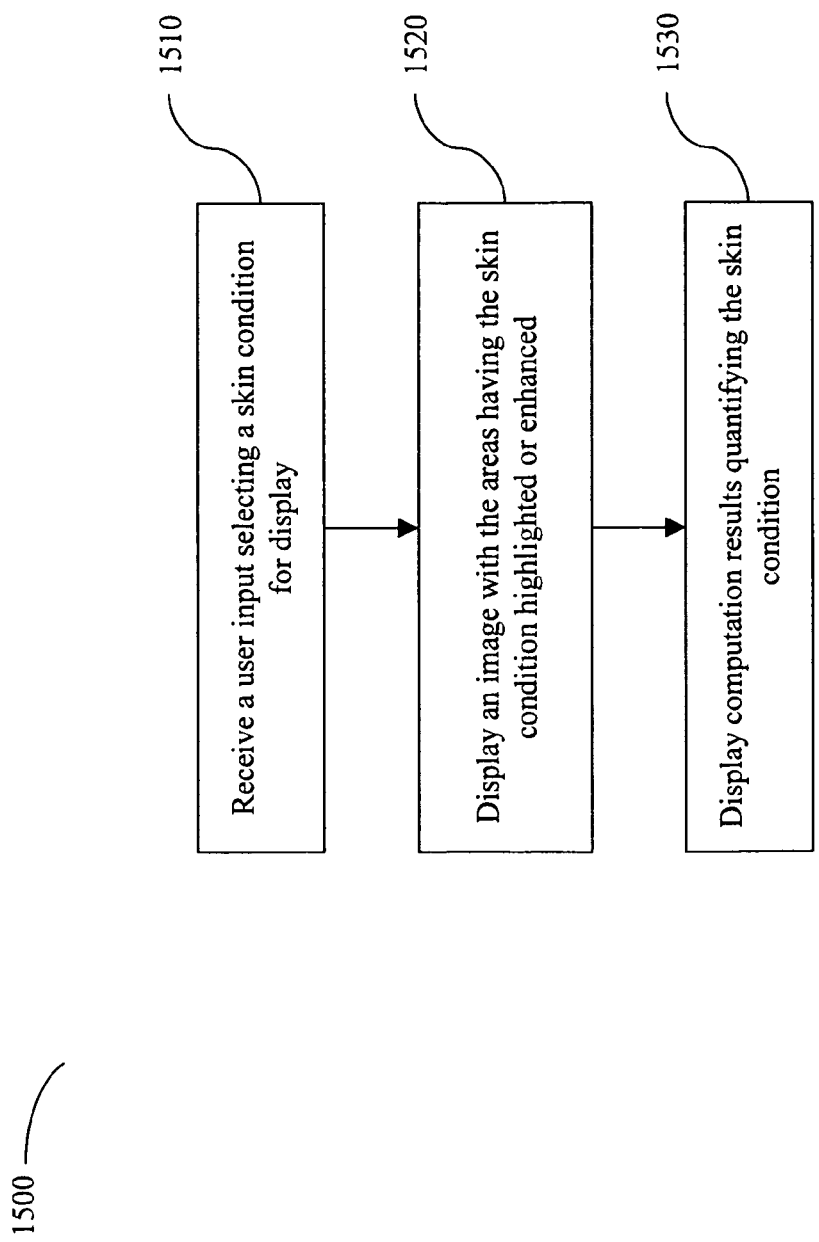
FIG. 15A is a flowchart illustrating process steps for displaying results of skin conditions according to one embodiment of the present invention.

In one embodiment, the module for outputting/displaying the results of skin analysis includes a submodule 1500 for displaying the results with a GUI. As shown in FIG. 15, submodule 1500 includes a step 1510 in which a user input selecting a skin condition for display is received through the GUI, a step 1520 in which an image having the selected skin condition highlighted or enhanced is displayed, and a step 1530 in which computation results quantifying the skin condition is displayed.

For example, assuming that the user has selected pores or a type of pores as the skin conditions for display, the GUI according to submodule 1500 may display a color image of the subject with all pores or the selected type of pores highlighted as, for example, bright white dots on the color image. Different pores may also be highlighted using different colors. At the same time or on the same screen, a pore count for all of the pores found, and/or for each of different types of pores are listed.

Figure 15B:
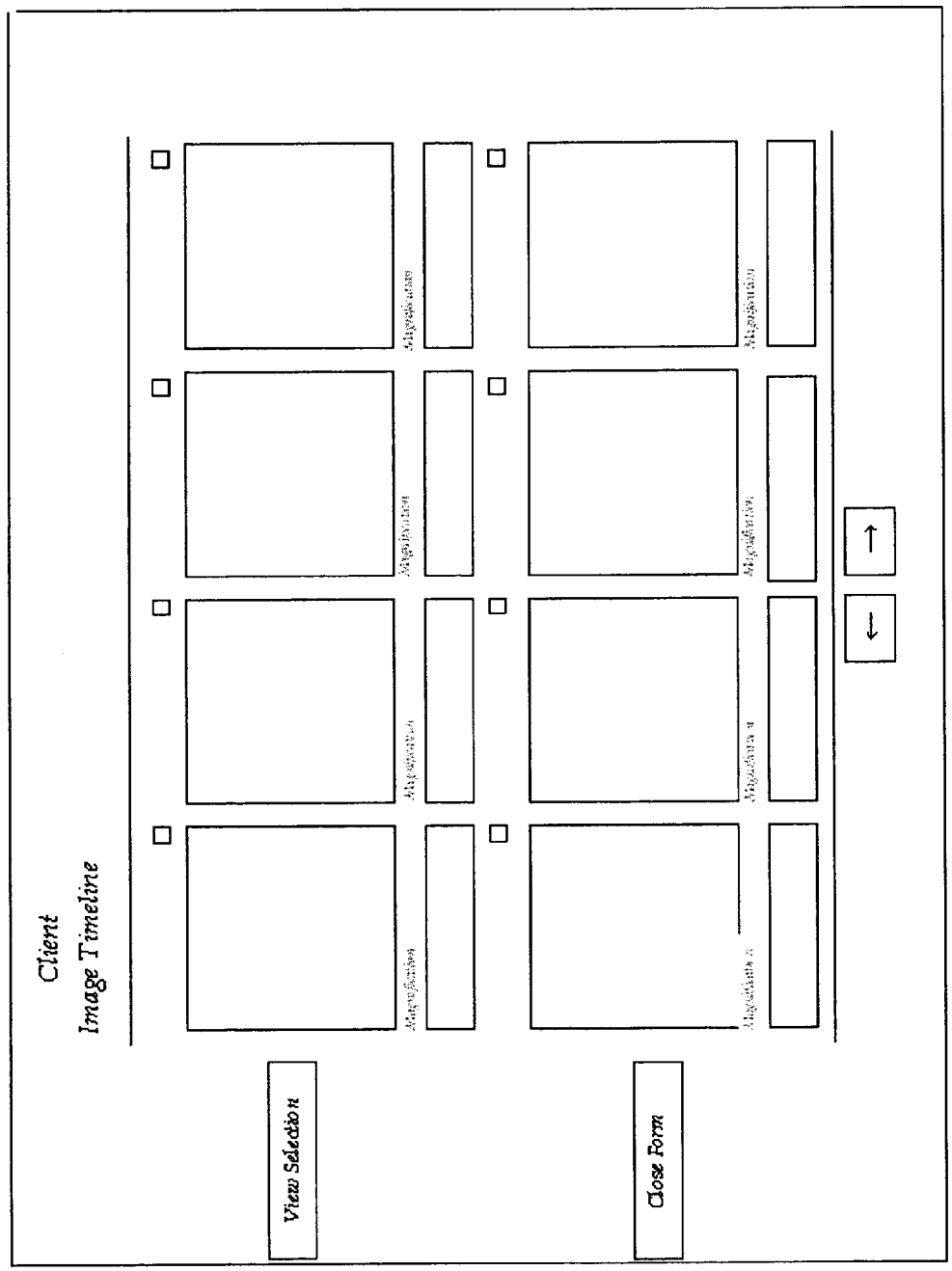
FIG. 15B is a line drawing of a user interface for displaying a timeline of results of skin conditions according to one embodiment of the present invention.
Figure 15C:
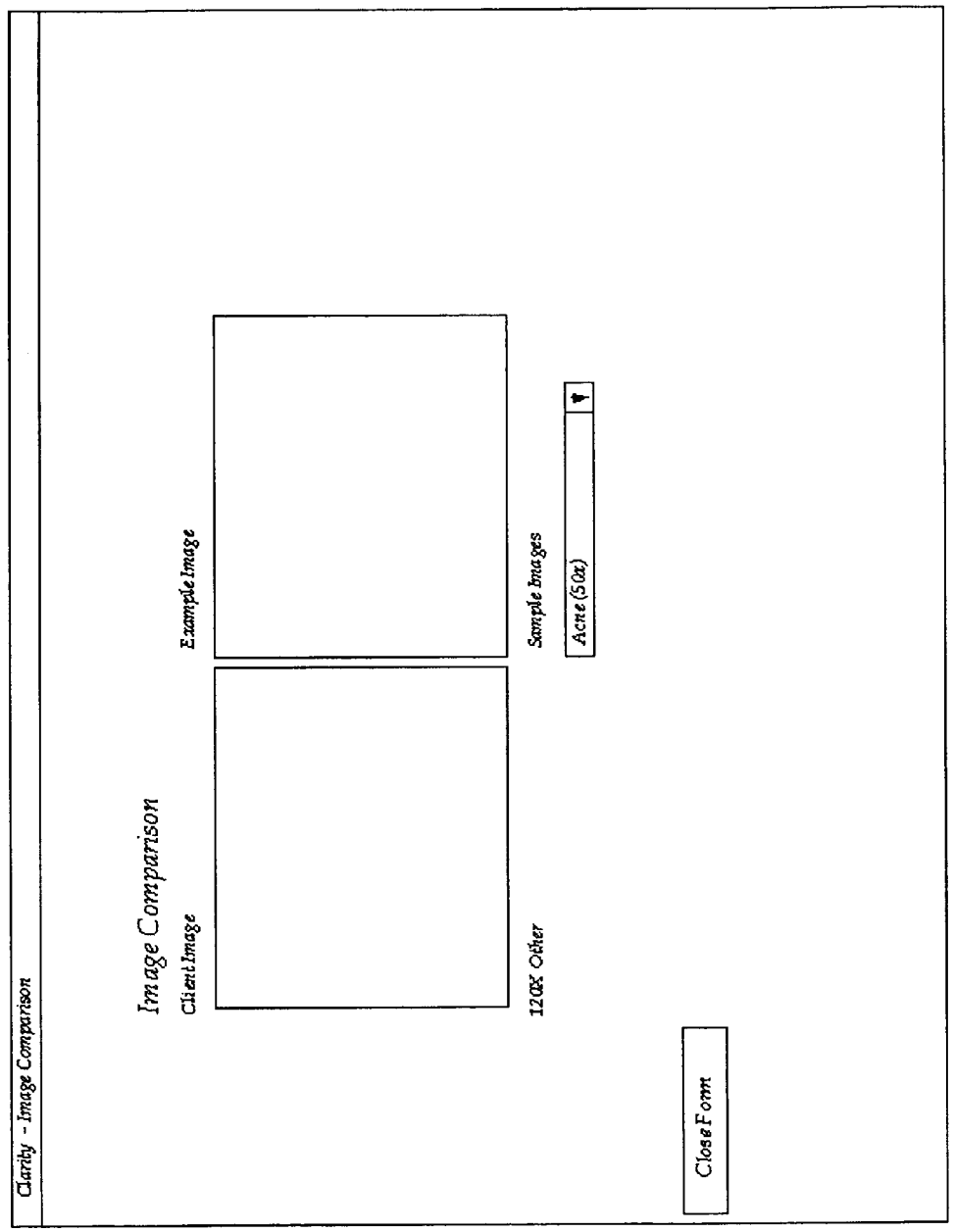
FIG. 15C is a line drawing of a user interface for displaying results related to a selected skin condition as compared with a previous results related to the same skin condition.
Figure 3:
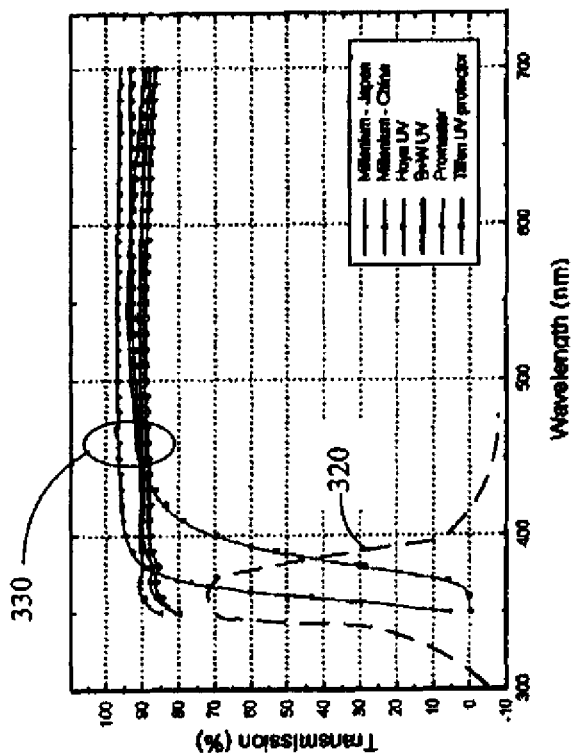
Figure 3:
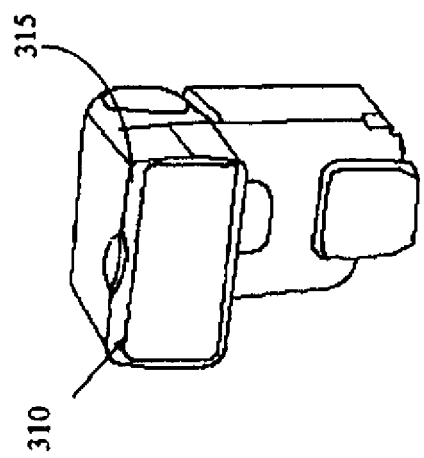

As shown in FIG. 15B, submodule 1500 may also display the skin analysis result in a timeline showing changes of selected skin analysis results over time for the same subject 101. As shown in FIG. 15C, submodule 1500 may also display selected skin analysis result as compared with previous results related to the same skin condition for the same subject 101.

The foregoing descriptions of specific embodiments of the present invention have been presented for purposes of illustration and description. They are not intended to be exhaustive or to limit the invention to the precise forms and procedures disclosed, and obviously many modifications and variations are possible in light of the above teaching. The embodiments were chosen and described in order to best explain the principles of the invention and its practical application, to thereby enable others skilled in the art to best use the teaching and various embodiments with various modifications as are suited to the particular use contemplated. It is intended that the scope of the invention be defined by the claims appended hereto and their equivalents.

We claim:

1. A method for analyzing skin conditions associated with a subject, comprising:
   acquiring a first white-light image and a first UV image of the subject, each of the first white-light and UV images include a plurality of pixels, each pixel in the first UV image corresponding to a respective pixel in the first white-light image;
   examining properties of each pixel in at least the first white-light image to identify skin-pixels in the first white-light and UV images; and
   obtaining results associated with at least one skin condition using information in the skin pixels in at least one of the first white-light and UV images.

2. The method of claim 1 wherein the first white-light and UV images are images of the face of a person.

3. The method of claim 1, wherein the step of acquiring comprises:
   applying UV light to the subject to acquire the first UV image; and
   applying white light to the subject to acquire the first white-light image.

4. The method of claim 3, further comprising placing a light-absorbing cloak to cover part of the subject before acquiring the first UV image.

5. The method of claim 1, further comprising orienting an image sensor to adjust an aspect ratio of each of the first white-light and UV images.

6. The method of claim 1, further comprising:
   generating a skin mask having a plurality of elements each corresponding to a respective pixel in the first white-light image and having been assigned a value;
   wherein the step of identifying comprises:
   for each pixel in the first white-light or UV image, determining if the pixel is a skin pixel by looking up the value in a corresponding element in the skin map.

7. The method of claim 6, wherein generating the skin mask comprises:
   converting the first white-light image into at least one second white-light image of at least one second color space, each pixel in the at least one second white-light image corresponding to a respective pixel in the first white-light-image and to a respective element in the skin mask; and
   for each element in the skin-mask:
   determining if pixel properties associated with the corresponding pixel in each of the white-light images satisfy predefined criteria for skin pixels associated with a respective color space; and
   assigning one of first and second values to the element.

8. The method of claim 7, wherein the step of assigning one of the first and second values comprises consulting a coordinate reference.

9. The method of claim 1, wherein the step of identifying comprises, for each pixel in the first white light image:
   determining if pixel values associated therewith satisfy a first set of predefined criteria for skin pixels.

10. The method of claim 9, wherein the first white-light image is of a first color space, and the step of identifying further comprises:
converting the first white-light image into at least one second white-light image of at least one second color space; and
for each of the at least one second image:
determining if pixel values associated with each of a plurality of pixels satisfy a respective set of predefined criteria for skin pixels.

11. The method of claim 9, wherein the step of identifying further comprises consulting a coordinate reference.

12. The method of claim 1, wherein the at least one skin condition is selected from a group consisting of: skin tone, UV damage, pores, wrinkles, hydration levels, collagen content, skin type, moles, pigmentation, and level of oil flow.

13. The method of claim 12, wherein the step of obtaining comprises using information in the skin pixels of one or both of the first white-light and UV images to obtain UV damage results associated with the subject.

14. The method of claim 13, wherein the information in each skin pixel of the white-light and UV images includes values associated with three color channels, and results associated with UV damage are obtained from values associated with one of the three color channels in the skin pixels of the first UV image.

15. The method of claim 12, wherein each skin pixel of the first white-light image includes values associated with three color channels, and the step of obtaining comprises using values associated with all of the three channels in the skin pixels of the white-light image to obtain the skin tone results that indicate an evenness of skin-tone associated with the subject.

16. The method of claim 15, wherein the step of obtaining further comprises computing a standard deviation for each of the three color channels.

17. The method of claim 12, wherein the step of obtaining comprises:
computing a color value and an intensity value associated with each of the skin pixels in the first UV image; and
for each skin pixel in the first UV image, determining if the color and intensity values fall within predetermined ranges for at least one skin condition.

18. The method of claim 17, wherein the step of obtaining further comprises:
for each skin pixel in the first UV image that has color and intensity values falling within predetermined ranges for a specified skin condition, determining a size of a skin area adjacent the skin pixel and having the specified skin condition by examining surrounding skin pixels for the specified skin condition.

19. The method of claim 17, wherein the specified skin condition is related to a specific type of pores, and the step of obtaining further comprises:
counting the skin areas having the specified skin condition to obtain a number of the specific type of pores.

20. The method of claim 17, wherein the at least one skin condition includes a plurality of types of pores, and the step of obtaining further comprises:
for each skin pixel in the first UV image that has color and intensity values falling within predetermined ranges for each of the plurality of types of pores, determining a size of a pore by examining surrounding skin pixels to determine if they belong to a same pore; and
counting the pores to obtain a pore count.

21. The method of claim 17, wherein the at least one skin condition includes at least one type of pores selected from the group consisting of: inflamed pores, bacteriostatic pores, sluggish oil flow, and deeply inflamed pores.

22. The method of claim 1, further comprising displaying results associated with at least one selected skin condition.

23. The method of claim 22, wherein the at least one selected skin condition includes pores, and the step of displaying comprises:
displaying on a user interface an image of the subject with at least one type of pores highlighted; and
displaying a pore count value indicating a number of at least one type of pores associated with the subject.

24. The method of claim 23, wherein at least two types of pores are highlighted in the image using different colors, each color corresponding to a respective type of pores.

25. The method of claim 23, wherein the at least one selected skin condition includes UV damage, and the step of displaying comprises:
displaying an image of the subject with areas having UV damage highlighted.

26. The method of claim 25, wherein each pixel in the first white-light and UV images includes values associated with first, second and third color channels, and the step of displaying the image of the subject comprises:
composing an image for display, said image for display having pixels each correspond to a respective pixel in the first white-light image and to a respective pixel in the first UV image;
for each pixel in the image for display, assign first, second, and third values to respective ones of the first, second, and third color channels in the pixel, the first and second values being proportional to respective ones of the values associated with the first and second color channels in the corresponding pixel of the first white-light image, and the third value being proportional to an average of the values associated with the third color channel in corresponding pixels of the first white-light and UV images.

27. The method of claim 22, wherein the step of displaying comprises displaying both current and prior results associated with at least one selected skin condition for the subject for comparison.

28. A computer readable medium storing therein program instructions that when executed by a processor cause the processor to perform a method for analyzing skin conditions associated with a subject, the program instructions comprising:
instructions for acquiring a first white-light image and a first UV image of the subject, each pixel in the first UV image corresponding to a respective pixel in the first white-light image;
instructions for identifying, on a pixel by pixel basis, skin-pixels in the first white-light and UV images; and
instructions for obtaining results associated with at least one skin condition using information in the skin pixels in the first white light and UV images.

29. The computer readable medium of claim 28, wherein the instructions for acquiring comprises instructions for acquiring the first white-light and UV images from a digital processor.

30. The computer readable medium of claim 28, wherein the instructions for identifying comprises:
instructions for generating a skin map that maps skin pixels in the first white-light and UV image.

31. The computer readable medium of claim 28, wherein the instructions for identifying comprises:

instructions for determining, for each pixel in the first white-light image, if the pixel is a skin pixel by referencing a skin map.

32. The computer readable medium of claim 28, wherein the instructions for obtaining comprises instructions for using information in the skin pixels of one or both of the first white-light and UV images to obtain UV damage results that quantify UV damage associated with the subject.

33. The computer readable medium of claim 32, wherein the information in each skin pixel of the white-light and UV images includes values associated with three color channels, and the UV damage results are computed based on values associated with one of the three color channels in the skin pixels of the first UV image.

34. The computer readable medium of claim 28, wherein each skin pixel of the first white-light image includes values associated with three color channels, and wherein the instructions for obtaining comprises using values associated with all of the three channels in the skin pixels of the white-light image to obtain the skin tone results that indicates an evenness of skin-tone associated with the subject.

35. The computer readable medium of claim 34, wherein the instructions for obtaining further comprises instructions for computing a standard deviation for each of the three color channels from values associated with a respective one of the three color channels.

36. The computer readable medium of claim 28, wherein the instructions for obtaining comprises:
   instructions for computing a color value and an intensity value associated with each of the skin pixels in the first UV image; and
   instructions for determining, for each skin pixel in the first UV image, if the color and intensity values fall within predetermined ranges for at least one skin condition.

37. A computer system including the computer readable medium of claim 28.

38. A system for analyzing skin conditions associated with a subject, comprising:
   an image acquisition device configured to acquire a first white-light image and a first UV image of the subject, each of the first white-light and UV images having a plurality of pixels, each pixel in the first UV image corresponding to a respective pixel in the first white-light image;
   a computer system configured to identify, on a pixel by pixel basis, skin-pixels in the first white-light and UV images, and to obtain results associated with at least one skin condition using information in the skin pixels in the first white light and UV images.

39. The system of claim 38, wherein the image acquisition device has a sensor that can be rotated to adjust an aspect ratio of the white-light or UV image according to control signals from the computer system.

40. The system of claim 38, wherein the image acquisition device comprises:
   a sensor;
   an optical assembly configured to form images of the subject on the sensor; and
   a plurality of flash light sources attached thereto, including two flash light sources on two sides of the optical assembly, and one on top of the optical assembly, at least a portion of the flash light sources have UV transmission filters installed thereon, and at least a portion of the flash light sources have infrared absorption filters installed thereon.

* * * * *

UNITED STATES PATENT AND TRADEMARK OFFICE
CERTIFICATE OF CORRECTION

PATENT NO. : 7,454,046 B2 Page 1 of 2
APPLICATION NO. : 11/232452
DATED : November 18, 2008
INVENTOR(S) : Rajeshwar Chhibber et al.

It is certified that error appears in the above-identified patent and that said Letters Patent is hereby corrected as shown below:

IN THE DRAWINGS

Replace FIG. 3 with enclosed corrected FIG. 3.

In Col. 1, line 22, change "heath care" to --health care--.

In Col. 7, line 28, change "the can causes" to --that can cause--.

Signed and Sealed this

Twenty-fourth Day of February, 2009

JOHN DOLL
*Acting Director of the United States Patent and Trademark Office*